US012740722B2

(12) United States Patent
Sarkar et al.

(10) Patent No.: US 12,740,722 B2
(45) **Date of Patent: *Sep. 22, 2026**

(54) SENSING RESPIRATION PARAMETERS BASED ON AN IMPEDANCE SIGNAL

(71) Applicant: Medtronic, Inc., Minneapolis, MN (US)

(72) Inventors: Shantanu Sarkar, Roseville, MN (US); Eric M. Christensen, Dedham, IA (US); Deborah Ann Jaye, Lino Lakes, MN (US); Niranjan Chakravarthy, Singapore (SG); Geert Morren, Vissenaken (BE); Jerry D. Reiland, Coon Rapids, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/652,729

(22) Filed: May 1, 2024

(65) Prior Publication Data

US 2024/0277236 A1 Aug. 22, 2024

Related U.S. Application Data

(63) Continuation of application No. 16/450,250, filed on Jun. 24, 2019, now Pat. No. 11,998,303.

(51) Int. Cl.

*A61B 5/08* (2006.01)
*A61B 5/00* (2006.01)
(Continued)

(52) U.S. Cl.

CPC .......... *A61B 5/0816* (2013.01); *A61B 5/0205* (2013.01); *A61B 5/1118* (2013.01); (Continued)

(58) Field of Classification Search

None
See application file for complete search history.

(56) References Cited

U.S. PATENT DOCUMENTS 4,305,400 A * 12/1981 Logan .................. A61B 5/0806 600/483
4,379,460 A 4/1983 Judell
(Continued)

OTHER PUBLICATIONS

Cohen et al., "Comparison of Impedance and Inductance Ventilation Sensors on Adults During Breathing, Motion, and Simulated Airway Obstruction," IEEE Transactions on Biomedical Engineering, vol. 44, No. 7, Jul. 1, 1997, 12 pp.
(Continued)

*Primary Examiner* — Jacqueline Cheng
*Assistant Examiner* — Samuel C Kim
(74) *Attorney, Agent, or Firm* — Shumaker & Sieffert, P.A.

(57) ABSTRACT

This disclosure is directed to devices, systems, and techniques for identifying a respiration rate based on an impedance signal. In some examples, a medical device system includes a medical device including a plurality of electrodes. The medical device is configured to perform, using the plurality of electrodes, an impedance measurement to collect a set of impedance values, where the set of impedance values is indicative of a respiration pattern of a patient. Additionally, the medical device system includes processing circuitry configured to identify a set of positive zero crossings based on the set of impedance values, identify a set of negative zero crossings based on the set of impedance values, and determine, for the impedance measurement, a value of a respiration metric using both the set of negative zero crossings and the set of positive zero crossings.

17 Claims, 15 Drawing Sheets

(51) Int. Cl.

| | |
|---|---|
| ***A61B 5/0205*** | (2006.01) |
| ***A61B 5/11*** | (2006.01) |
| ***A61B 5/364*** | (2021.01) |
| *A61B 5/024* | (2006.01) |
| *A61B 5/085* | (2006.01) |

(52) U.S. Cl.

CPC ............ *A61B 5/364* (2021.01); *A61B 5/4561* (2013.01); *A61B 5/024* (2013.01); *A61B 5/086* (2025.01); *A61B 2562/0204* (2013.01)

(56) References Cited

U.S. PATENT DOCUMENTS

| | | | | |
|---|---|---|---|---|
| 4,411,267 | A | 10/1983 | Heyman | |
| 5,143,078 | A | 9/1992 | Mather et al. | |
| 5,201,808 | A | 4/1993 | Steinhaus et al. | |
| 5,300,093 | A | 4/1994 | Koestner et al. | |
| 5,412,730 | A | 5/1995 | Jones | |
| 5,687,722 | A | 11/1997 | Tien et al. | |
| 5,792,065 | A | 8/1998 | Xue et al. | |
| 5,824,020 | A | 10/1998 | Cooper | |
| 5,876,353 | A | 3/1999 | Riff | |
| 6,128,584 | A | 10/2000 | Hemminger et al. | |
| 7,094,207 | B1 | 8/2006 | Koh | |
| 7,371,220 | B1 | 5/2008 | Koh et al. | |
| 7,725,172 | B2 | 5/2010 | Rouw et al. | |
| 8,202,224 | B2 | 6/2012 | Gutfinger et al. | |
| 8,209,033 | B2 | 6/2012 | Zhang et al. | |
| 8,255,046 | B2 | 8/2012 | Sarkar et al. | |
| 8,886,296 | B2 | 11/2014 | Patel | |
| 8,914,106 | B2 | 12/2014 | Charlton et al. | |
| 8,942,795 | B2 | 1/2015 | Gunderson et al. | |
| 9,339,209 | B2 | 5/2016 | Banet et al. | |
| 9,597,525 | B2 | 3/2017 | Cao et al. | |
| 9,649,496 | B2 | 5/2017 | Thakur et al. | |
| 9,713,701 | B2 | 7/2017 | Sarkar et al. | |
| 10,596,381 | B2 | 3/2020 | Averina et al. | |
| 10,750,996 | B2 | 8/2020 | Wariar | |
| 10,893,824 | B2 | 1/2021 | An et al. | |
| 10,952,681 | B2 | 3/2021 | Sharma et al. | |
| 2002/0072685 | A1 | 6/2002 | Rymut et al. | |
| 2002/0183644 | A1 | 12/2002 | Levendowski et al. | |
| 2004/0220631 | A1 | 11/2004 | Burnes et al. | |
| 2006/0116592 | A1 | 6/2006 | Zhou et al. | |
| 2006/0206157 | A1* | 9/2006 | Hoijer | A61N 1/36521 607/17 |
| 2006/0264776 | A1 | 11/2006 | Stahmann et al. | |
| 2006/0276848 | A1 | 12/2006 | Min et al. | |
| 2007/0118183 | A1* | 5/2007 | Gelfand | A61N 1/3614 607/42 |
| 2007/0239057 | A1 | 10/2007 | Pu et al. | |
| 2008/0082003 | A1* | 4/2008 | Deng | A61B 5/0816 600/529 |
| 2008/0228094 | A1* | 9/2008 | Audet | A61B 5/33 600/513 |
| 2008/0234599 | A1 | 9/2008 | Chiao et al. | |
| 2008/0319333 | A1 | 12/2008 | Gavish et al. | |
| 2009/0198139 | A1 | 8/2009 | Lewicke et al. | |
| 2010/0030292 | A1 | 2/2010 | Sarkar et al. | |
| 2010/0113962 | A1 | 5/2010 | Hettrick et al. | |
| 2010/0152600 | A1 | 6/2010 | Droitcour et al. | |
| 2010/0198097 | A1 | 8/2010 | Sowelam | |
| 2010/0317986 | A1* | 12/2010 | Colman | A61B 5/082 600/532 |
| 2011/0066062 | A1 | 3/2011 | Banet et al. | |
| 2011/0190654 | A1 | 8/2011 | Hettrick et al. | |
| 2011/0224520 | A1* | 9/2011 | Skerl | A61B 5/0295 600/377 |
| 2011/0230779 | A1 | 9/2011 | Titchener | |
| 2011/0245700 | A1 | 10/2011 | Ghanem et al. | |
| 2012/0197088 | A1 | 8/2012 | Karamanoglu et al. | |
| 2013/0079646 | A1 | 3/2013 | Bhunia et al. | |
| 2013/0197386 | A1* | 8/2013 | Cho | A61B 5/0538 600/533 |
| 2014/0073898 | A1 | 3/2014 | Engelbrecht et al. | |
| 2014/0088450 | A1 | 3/2014 | Mottaiyan et al. | |
| 2014/0276928 | A1 | 9/2014 | Vanderpool et al. | |
| 2015/0283381 | A1* | 10/2015 | Denk | A61B 5/4818 607/42 |
| 2016/0114168 | A1 | 4/2016 | Demmer et al. | |
| 2016/0310031 | A1 | 10/2016 | Sarkar | |
| 2017/0021489 | A1 | 1/2017 | Bylund et al. | |
| 2017/0354365 | A1 | 12/2017 | Zhou | |
| 2018/0028824 | A1 | 2/2018 | Pivonka | |
| 2018/0028828 | A1 | 2/2018 | Cao et al. | |
| 2018/0168461 | A1 | 6/2018 | Morris et al. | |
| 2018/0168463 | A1 | 6/2018 | Morris et al. | |
| 2018/0325420 | A1* | 11/2018 | Gigi | A61B 5/6823 |
| 2019/0059816 | A1 | 2/2019 | Katra et al. | |
| 2019/0070419 | A1* | 3/2019 | Virtanen | A61B 5/7217 |
| 2020/0030612 | A1 | 1/2020 | Song et al. | |
| 2020/0054238 | A1 | 2/2020 | Gopinathan et al. | |
| 2020/0397308 | A1 | 12/2020 | Sarkar et al. | |
| 2021/0020294 | A1 | 1/2021 | Bharmi et al. | |
| 2021/0093220 | A1 | 4/2021 | Sarkar et al. | |
| 2021/0093253 | A1 | 4/2021 | Sarkar et al. | |
| 2021/0093254 | A1 | 4/2021 | Sarkar et al. | |
| 2021/0204874 | A1 | 7/2021 | Thakur et al. | |
| 2021/0345935 | A1 | 11/2021 | Gill et al. | |
| 2024/0138737 | A1 | 5/2024 | Sarjar et al. | |

OTHER PUBLICATIONS

International Search Report and Written Opinion of International Application No. PCT/US2020/036917, mailed Sep. 21, 2020, 10 pp.

Prosecution History from U.S. Appl. No. 16/450,250, dated Aug. 4, 2021 through Feb. 2, 2024, 515 pp.

Giraud et al., "Respiratory change in ECG-wave amplitude is a reliable parameter to estimate intravascular volume status", Journal of clinical monitoring and computing, Springer Science+Business Media, Nov. 2, 2012, pp. 107-111.

Lara et al., "Accurate monitoring of intravascular fluid volume: A novel application of intrathoracic impedance measures for the guidance of volume reduction therapy", IJC Heart & Vasculature, vol. 8, Elsevier Ireland Ltd., May 15, 2015, pp. 47-51.

Maisel, "B-Type Natriuretic Peptide Levels: Diagnostic and Prognostic in Congestive Heart Failure What's Next?", American Heart Association, Inc., vol. 105, No. 20, May 21, 2002, pp. 2328-2331.

Montgomery et al., "Monitoring intracellular, interstitial, and intravascular vol. changes during fluid management procedures", Medical & biological engineering & computing, Oct. 1, 2013, pp. 1167-1175.

Thakur et al., "Haemodynamic monitoring of cardiac status using heart sounds from an implanted cardiac device", ESC heart failure, vol. 4, No. 4, Jul. 4, 2017, pp. 605-613.

First Examination Report from counterpart Australian Application No. 2020308341 dated Feb. 18, 2025, 3 pp.

* cited by examiner

FIG. 8

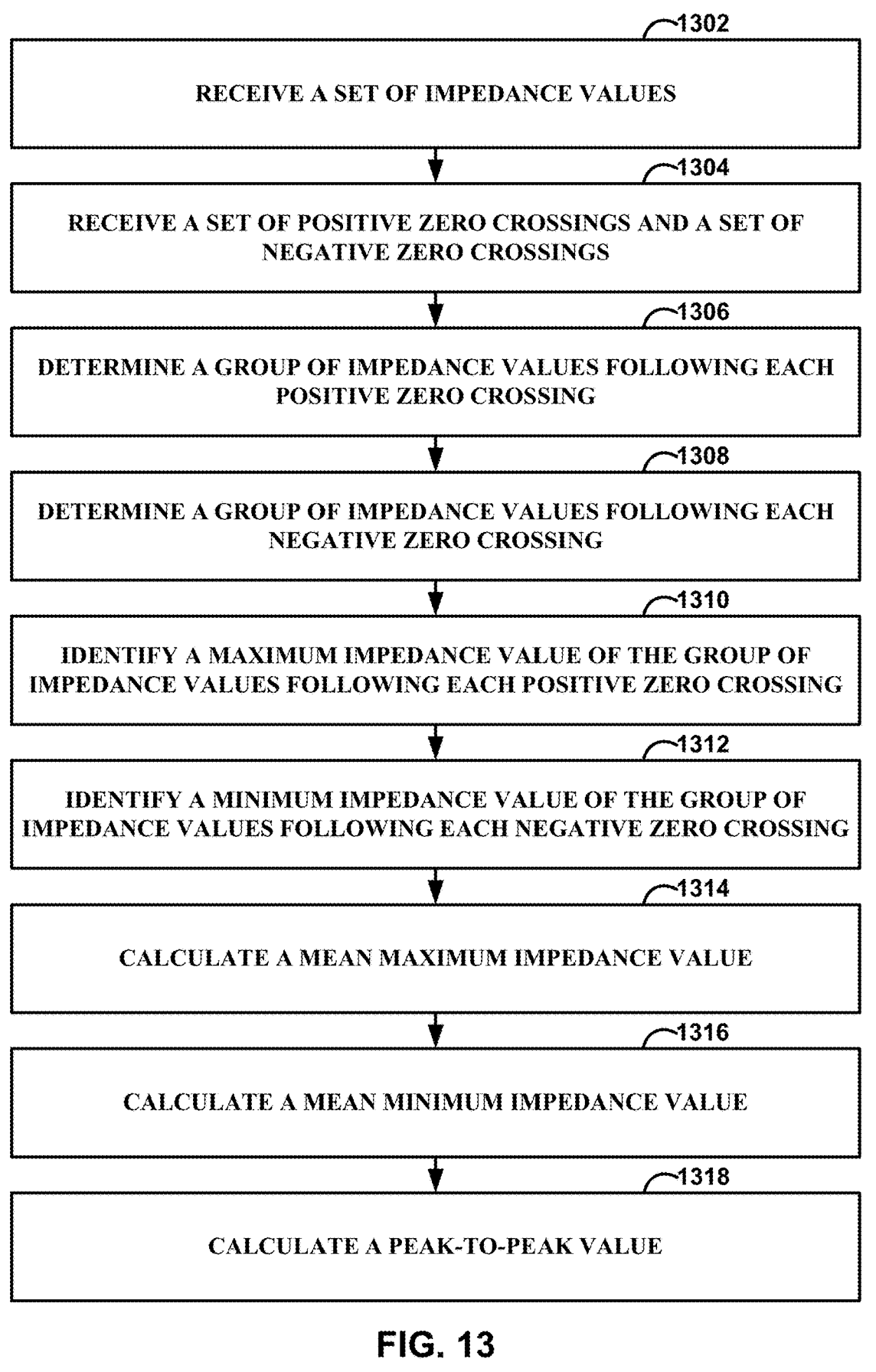

1302 RECEIVE A SET OF IMPEDANCE VALUES

1304 RECEIVE A SET OF POSITIVE ZERO CROSSINGS AND A SET OF NEGATIVE ZERO CROSSINGS

1306 DETERMINE A GROUP OF IMPEDANCE VALUES FOLLOWING EACH POSITIVE ZERO CROSSING

1308 DETERMINE A GROUP OF IMPEDANCE VALUES FOLLOWING EACH NEGATIVE ZERO CROSSING

1310 IDENTIFY A MAXIMUM IMPEDANCE VALUE OF THE GROUP OF IMPEDANCE VALUES FOLLOWING EACH POSITIVE ZERO CROSSING

1312 IDENTIFY A MINIMUM IMPEDANCE VALUE OF THE GROUP OF IMPEDANCE VALUES FOLLOWING EACH NEGATIVE ZERO CROSSING

1314 CALCULATE A MEAN MAXIMUM IMPEDANCE VALUE

1316 CALCULATE A MEAN MINIMUM IMPEDANCE VALUE

1318 CALCULATE A PEAK-TO-PEAK VALUE

FIG. 13

SENSING RESPIRATION PARAMETERS BASED ON AN IMPEDANCE SIGNAL

This application is a continuation of U.S. patent application Ser. No. 16/450,250, filed Jun. 24, 2019, the entire content of which is incorporated herein by reference.

TECHNICAL FIELD

The disclosure relates generally to medical device systems and, more particularly, medical device systems configured to monitor patient parameters.

BACKGROUND

Some types of medical devices may be used to monitor one or more physiological parameters of a patient. Such medical devices may include, or may be part of a system that includes, sensors that detect signals associated with such physiological parameters. Values determined based on such signals may be used to assist in detecting changes in patient conditions, in evaluating the efficacy of a therapy, or in generally evaluating patient health.

SUMMARY

In general, the disclosure is directed to devices, systems, and techniques for using a medical device to perform an impedance measurement indicative of a respiratory parameter of a patient. The impedance of an electrical path between electrodes of the medical device, in some cases, may represent a resistance associated with contact between the electrodes and target tissue of the patient, and/or the impedance of the tissue in the path between the electrodes. As such, impedance may change over a period of time according to movements of the patient and/or changes in the impedance of patient tissue. For example, as the patient's chest cavity moves during a respiration cycle, contact between the electrodes and the target tissue may change, thus causing impedance to change. Furthermore, the relative fluid content of the tissue within the path may change during the respiration cycle.

In some cases, the impedance may change according to a periodic function corresponding to respiratory cycles (e.g., breathing in and breathing out) performed by the patient. In this way, processing circuitry may analyze an impedance signal obtained by the medical device to identify parameters associated with the patient's respiratory cycles, such as respiratory rate, respiratory rate variability, and respiratory effort, as examples. Such parameters may in turn be analyzed, e.g., by the processing circuitry and/or a clinician, to identify or monitor patient conditions (e.g., heart failure, sleep apnea, or chronic obstructive pulmonary disease (COPD)).

The medical device may, in some examples, perform a set of impedance measurements. In some cases, the medical device may perform the set of impedance measurements at a measurement rate (e.g., one measurement per hour, one measurement per day, one measurement per month, or any other valid rate). In this way, the set of impedance measurements may present a detailed picture of the patient's respiratory patterns over an extended period of time, enabling processing circuitry to identify trends in the impedance data or otherwise analyze the impedance data to identify or monitor the patient conditions. In some cases, the medical device may keep track of times in which particular impedance measurements are performed, so that the impedance data may be analyzed based on times of day in which the measurements occur (e.g., daytime vs. nighttime). Although, in some cases, the medical device may be configured consistently to perform the set of impedance measurements at the measurement rate, in other cases, the medical device may measure one or more patient parameters to determine whether to perform an impedance measurement, or measure one or more patient parameters to determine whether an impedance measurement produces adequate data. For example, prior to performing an impedance measurement, the medical device may perform an activity level measurement to determine a motion level of the patient. If the motion level is lower than a motion level threshold, the medical device may determine that conditions are adequate to perform an impedance measurement. Additionally, in some examples, the medical device may determine whether to perform impedance measurements based on a heart rate, a patient posture (e.g., sitting, standing, or laying down), an electrocardiogram (ECG), a presence or an absence of one or more arrhythmias, patient triggers, or acoustic data. In general, the medical device may monitor such parameters to ensure that physiological condition of the patient will be similar between measurements and/or to avoid measuring impedance when the patient condition is likely to result in noise (e.g., non-respiration variations) within the impedance signal.

To determine a respiratory rate of the patient during a particular impedance measurement, processing circuitry may be configured to process the impedance signal corresponding to the impedance measurement to identify a set of respiratory intervals. Each respiratory interval of the set of respiratory intervals may represent a full respiratory cycle (e.g. a combination of an exhaling phase and an inhaling phase). For example, in order to identify the set of respiratory intervals, the processing circuitry may calculate a derivative of the impedance signal. Subsequently, in some cases, the processing circuitry is configured to identify a set of positive-going-negative zero crossings and a set of negative-going-positive zero crossings in the impedance signal, based on the impedance signal and a derivative of the impedance signal. Based on the set of positive-going-negative zero crossings and the set of negative-going-positive zero crossings, the processing circuitry may, in some cases, identify the set of respiratory intervals and calculate the respiration rate based on the set of respiratory intervals.

The techniques of this disclosure may provide one or more advantages. For example, being configured to identify positive-going-negative zero crossings and negative-going-positive zero crossings of the impedance signal may improve the accuracy with which the processing circuitry may determine a respiration rate based on data corresponding to an impedance measurement from the medical device. In some examples, the processing circuitry may determine a first set of respiratory intervals representing a period of time separating each pair of consecutive positive-going-negative zero crossings and a second set of respiratory intervals representing a period of time separating each pair of consecutive negative-going-positive zero crossings. This may increase a number of respiratory intervals for analysis, thus improving an accuracy of the calculated reparation rate. Additionally, in some examples, by performing impedance measurements based on a patient motion level, the medical device may avoid including impedance measurements performed while the patient condition is likely to result in noise in the impedance signal in the respiration parameter analysis, which may improve an ability of the medical device system to identify or monitor patient conditions.

In some examples, a medical device system includes a medical device including a plurality of electrodes, the medical device configured to perform, using the plurality of electrodes, an impedance measurement to collect a set of impedance values, where the set of impedance values is indicative of a respiration pattern of a patient. Additionally, the medical device system includes processing circuitry configured to identify a set of positive zero crossings based on the set of impedance values, identify a set of negative zero crossings based on the set of impedance values, and determine, for the impedance measurement, a value of a respiration metric using both the set of negative zero crossings and the set of positive zero crossings.

In some examples, a method includes performing, using a plurality of electrodes of a medical device, an impedance measurement to collect a set of impedance values, wherein the set of impedance values is indicative of a respiration pattern of a patient, identifying, using processing circuitry, a set of positive zero crossings based on the set of impedance values, identifying, using the processing circuitry, a set of negative zero crossings based on the set of impedance values, and determining, for the impedance measurement, a value of a respiration metric using both the set of negative zero crossings and the set of positive zero crossings.

In some examples, a non-transitory computer-readable medium stores instructions for causing processing circuitry to perform a method including performing, using a plurality of electrodes of a medical device, an impedance measurement to collect a set of impedance values, where the set of impedance values is indicative of a respiration pattern of a patient, identifying, using processing circuitry, a set of positive zero crossings based on the set of impedance values, identifying, using the processing circuitry, a set of negative zero crossings based on the set of impedance values, and determining, for the impedance measurement, a value of a respiration metric using both the set of negative zero crossings and the set of positive zero crossings.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

FIG. 8 is a flow diagram illustrating an example operation for performing parameter measurements, in accordance with one or more techniques of this disclosure.

FIG. 13 is a flow diagram illustrating an example operation for determining a peak-to-peak value, in accordance with one or more techniques of this disclosure.

Like reference characters denote like elements throughout the description and figures.

DETAILED DESCRIPTION

Figure 1:
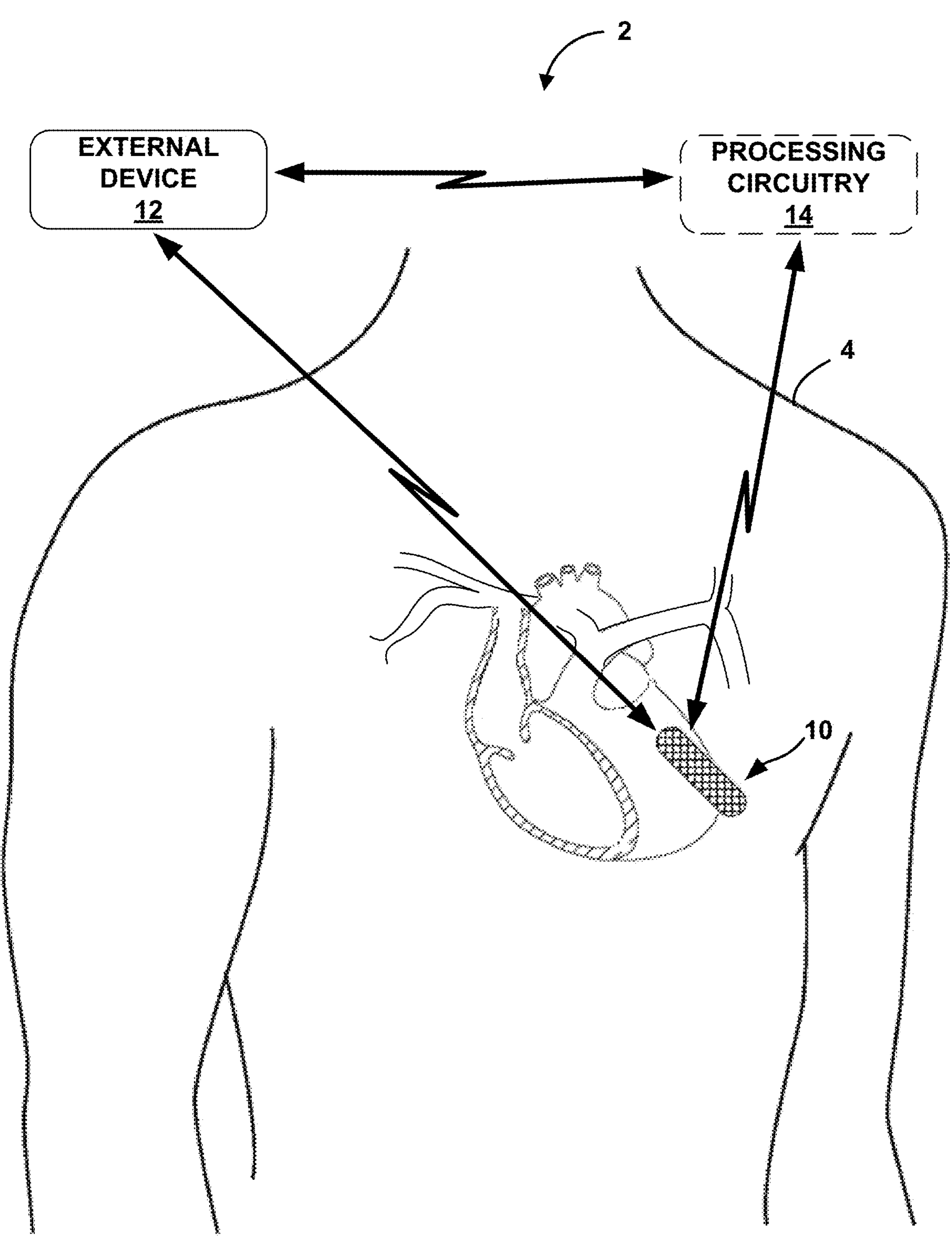
FIG. 1 illustrates the environment of an example medical device system in conjunction with a patient, in accordance with one or more techniques of this disclosure.

This disclosure describes techniques for performing parameter measurements and analyzing data corresponding to the parameter measurements in order to determine one or more parameter values. For example, an implantable medical device (IMD) may perform a set of impedance measurements to obtain impedance data. Processing circuitry, such as processing circuitry of the IMD, processing circuitry of an external programming device, processing circuitry of another device, or any combination thereof may analyze the impedance data in order to identify or monitor a medical condition of a patient. In some examples, the medical condition may include a respiratory condition such as sleep apnea or chronic obstructive pulmonary disease (COPD). Additionally, in some cases, the impedance data may be analyzed to distinguish between different types of breathing (e.g., eupnea (normal breathing), apnea, Cheyne-Stokes breathing, dyspnea, hyperpnea, hyperventilation, hypopnea, hypoventilation, tachypnea, or any combination thereof). In some examples, impedance data may be analyzed to monitor an exacerbation in a patient condition such as heart failure and impedance data may be analyzed to assist in differential diagnosis of a patient condition that leads to a change in at least one respiratory parameter (e.g., respiration rate, respiration variability, and respiration effort).

In some examples, impedance data collected by the IMD reflects, among other things, respiratory cycles of the patient. For example, during each impedance measurement of the set of impedance measurements, the IMD may measure an impedance corresponding to a resistance of a contact between one or more electrodes of the IMD and target tissue of the patient. As such, impedance values may be given by units of resistance (ohms (52)). As the patient inhales and exhales while the IMD performs an impedance measurement, thus moving the chest cavity, a nature of contact between the one or more electrodes and the target tissue may change, in some examples. Additionally, in some examples, movements of the chest cavity may cause a fluid content of the tissue proximate to IMD 10 to change. Consequently, impedance data may reflect the inhaling and the exhaling of the patient, and the impedance data may be analyzed to determine one or more respiratory parameters such as respiration rate, respiration rate variability, and respiration effort.

Components of the IMD may be powered by a power source, such as a battery, that has a limited amount of charge. Impedance measurements may cause components of the IMD to consume energy from the power source. As such, it may be beneficial to limit a number of impedance measurements or limit a length of the impedance measurements in order to preserve the charge of the power source while collecting enough impedance data to adequately identify or monitor a medical condition of the patient. In some examples, the IMD may perform the set of impedance measurements at a measurement rate. In some examples, the measurement rate is determined based on user input to an external device (e.g., a clinician programmer), and uploaded to the IMD via a wireless communication link. Additionally, each impedance measurement may last for a measurement duration. In some examples, the IMD may be configured to perform impedance measurements only during nighttime or only during daytime. In some examples, the IMD performs impedance measurements according to a custom schedule that is uploaded to the IMD from an external device and executed by the IMD. Additionally, in some examples, the IMD may perform a one-time impedance measurement based on an instruction received from an external device, e.g., from a patient or clinician.

In some examples, the IMD may be configured to perform impedance measurements based on one or more "triggers." Such triggers may include a patient motion level falling below a motion level threshold or within a motion level range. Other triggers may include parameters such as heart rate, patient posture, ECG, arrhythmias, patient triggers, and acoustic data. For example, the IMD may perform an impedance measurement in response to a change in patient posture, a change in heart rate, or a detection of a sounds (e.g., snoring) indicative of a medical condition such as sleep apnea. In some examples, impedance measurement triggers may involve a combination of parameters (e.g., trigger activates due to a change in patient posture and a change in heart rate). Additionally, in some examples, an impedance measurement may be triggered in response to an identified pattern in one or more parameters (e.g., a period of relatively low patient motion following a period of relatively high patient motion).

During an impedance measurement the IMD may, in some examples, filter the collected impedance data to extract a respiratory component of the impedance data. For example, the IMD may apply a high-pass filter and a low-pass filter to the impedance data, thus attenuating higher-frequency components and lower-frequency components of the impedance data that may be related to cardiac functions, intestinal functions, or other functions not related to respiratory cycles of the patient. In this manner, the IMD may pre-process the impedance data to produce filtered impedance data that reflects respiratory cycles of the patient. In addition to filtering the impedance data using a high-pass filter and a low-pass filter, in some examples, the IMD may down-sample the impedance data to decrease a sampling frequency of the impedance data.

Once the filtered impedance data is generated by the IMD during the set of impedance measurements, the impedance data may be processed and analyzed to identify or monitor medical conditions in the patient. For example, processing circuitry of the IMD, processing circuitry of an external programmer, processing circuitry of another device, or any combination thereof may process the filtered impedance data to determine a set of respiratory parameters including any combination of a respiration rate, a respiration rate variability, and a respiration effort. In some examples, for each impedance measurement, the IMD may determine a set of respiratory intervals, where each respiratory interval represents a full respiratory cycle of inhaling and exhaling. Based on the set of respiratory intervals, the processing circuitry may calculate a mean respiratory interval. Based on the mean respiratory interval, the IMD may calculate the respiration rate corresponding to the respective impedance measurement. Additionally, in some examples, based on the set of respiratory intervals, the IMD may determine a respiratory rate variability. Respiration effort may, in some cases, be represented by a difference between a maximum impedance value and a minimum impedance value in a particular respiratory cycle. In some cases, respiration effort is represented by a mean difference between respective maximum impedance values and respective minimum impedance values corresponding to a set of respiratory cycles.

FIG. 1 illustrates the environment of an example medical device system 2 in conjunction with a patient 4, in accordance with one or more techniques of this disclosure. The example techniques may be used with an IMD 10, which may be in wireless communication with at least one of external device 12 and other devices not pictured in FIG. 1. For example, an external device (not pictured in FIG. 1) may include at least a portion of processing circuitry 14, the external device configured for communication with IMD 10 and external device 12. In some examples, IMD 10 is implanted outside of a thoracic cavity of patient 4 (e.g., subcutaneously in the pectoral location illustrated in FIG. 1). IMD 10 may be positioned near the sternum near or just below the level of patient 4's heart, e.g., at least partially within the cardiac silhouette. In some examples, IMD 10 takes the form of a LINQ™ Insertable Cardiac Monitor (ICM), available from Medtronic plc, of Dublin, Ireland.

Clinicians sometimes diagnose patients with medical conditions based on one or more observed physiological signals collected by physiological sensors, such as electrodes, optical sensors, chemical sensors, temperature sensors, acoustic sensors, and motion sensors. In some cases, clinicians apply non-invasive sensors to patients in order to sense one or more physiological signals while a patent is in a clinic for a medical appointment. However, in some examples, physiological markers (e.g., irregular heartbeats and long-term respiration trends) of a patient condition are rare or are difficult to observe over a relatively short period of time. As such, in these examples, a clinician may be unable to observe the physiological markers needed to diagnose a patient with a medical condition while monitoring one or more physiological signals of the patient during a medical appointment. In the example illustrated in FIG. 1, IMD 10 is implanted within patient 4 to continuously record one or more physiological signals of patient 4 over an extended period of time.

In some examples, IMD 10 includes a plurality of electrodes. The plurality of electrodes is configured to detect signals that enable processing circuitry of IMD 10 to determine current values of additional parameters associated with the cardiac and/or lung functions of patient 4. In some examples, the plurality of electrodes of IMD 10 are configured to detect a signal indicative of an electric potential of the tissue surrounding the IMD 10. Moreover, IMD 10 may additionally or alternatively include one or more optical sensors, accelerometers, temperature sensors, chemical sensors, light sensors, pressure sensors, in some examples. Such sensors may detect one or more physiological parameters indicative of a patient condition.

External device 12 may be a hand-held computing device with a display viewable by the user and an interface for providing input to external device 12 (i.e., a user input mechanism). For example, external device 12 may include a small display screen (e.g., a liquid crystal display (LCD) or a light emitting diode (LED) display) that presents information to the user. In addition, external device 12 may include a touch screen display, keypad, buttons, a peripheral pointing device, voice activation, or another input mechanism that allows the user to navigate through the user interface of external device 12 and provide input. If external device 12 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, external device 12 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure device.

When external device 12 is configured for use by the clinician, external device 12 may be used to transmit instructions to IMD 10. Example instructions may include requests to set electrode combinations for sensing and any other information that may be useful for programming into IMD 10. The clinician may also configure and store operational parameters for IMD 10 within IMD 10 with the aid of external device 12. In some examples, external device 12 assists the clinician in the configuration of IMD 10 by providing a system for identifying potentially beneficial operational parameter values.

Whether external device 12 is configured for clinician or patient use, external device 12 is configured to communicate with IMD 10 and, optionally, another computing device (not illustrated in FIG. 1), via wireless communication. External device 12, for example, may communicate via near-field communication technologies (e.g., inductive coupling, NFC or other communication technologies operable at ranges less than 10-20 cm) and far-field communication technologies (e.g., RF telemetry according to the 802.11 or Bluetooth® specification sets, or other communication technologies operable at ranges greater than near-field communication technologies).

Processing circuitry 14, in some examples, may include one or more processors that are configured to implement functionality and/or process instructions for execution within IMD 10. For example, processing circuitry 14 may be capable of processing instructions stored in a storage device. Processing circuitry 14 may include, for example, microprocessors, digital signal processors (DSPs), application specific integrated circuits (ASICs), field-programmable gate arrays (FPGAs), or equivalent discrete or integrated logic circuitry, or a combination of any of the foregoing devices or circuitry. Accordingly, processing circuitry 14 may include any suitable structure, whether in hardware, software, firmware, or any combination thereof, to perform the functions ascribed herein to processing circuitry 14.

Processing circuitry 14 may represent processing circuitry located within any combination of IMD 10 and external device 12. In some examples, processing circuitry 14 may be entirely located within a housing of IMD 10. In other examples, processing circuitry 14 may be entirely located within a housing of external device 12. In other examples, processing circuitry 14 may be located within any combination of IMD 10, external device 12, and another device or group of devices that are not illustrated in FIG. 1. As such, techniques and capabilities attributed herein to processing circuitry 14 may be attributed to any combination of IMD 10, external device 12, and other devices that are not illustrated in FIG. 1.

IMD 10 may collect physiological signals that are indicative of respiratory parameters corresponding to patient 4. For example, the electrodes of IMD 10 may be configured to detect an electrical impedance signal which may be processed to determine one or more respiratory parameter values such as respiration rate, respiration rate variability, and respiration effort. Electrical impedance, in some cases, may be a measure of a resistance associated with contact between electrodes and various surfaces. For example, IMD 10 may be configured to measure an impedance corresponding to a contact between one or more electrodes of IMD 10 and target tissue of patient 4. Since patient 4 moves, a nature of the contact (e.g., a fluid content of tissue proximate to IMD 10) between the one or more electrodes and the target tissue may change over a period of time. For example, the fluid content of tissue proximate to IMD 10 may fluctuate due to a change in intrathoracic pressure during the respiratory cycle caused by venous return, thus causing the fluid content around the electrodes and the nature of the contact between the one or more electrodes and the target tissue to fluctuate accordingly. In this manner, as patient 4 inhales and exhales during a series of respiratory cycles causing patient 4's chest cavity to expand and retract, the impedance signal measured by IMD 10 may reflect such expansions and retractions of the chest cavity. Processing circuitry 14 may be configured to analyze the impedance signal to determine the one or more respiratory parameters based on the relationship between the impedance signal and respiratory patterns of patient 4.

IMD 10 may be configured to perform a series of impedance measurements over a period of time in order to obtain impedance data such that trends of respiratory parameter values may be observed. In some examples, IMD 10 may perform a set of impedance measurements at a measurement rate (e.g., one impedance measurement per hour, one impedance measurement per day, one impedance measurement per month, or any other valid rate). The measurement rate may, in some examples, be determined based on user input to external device 12 and uploaded to IMD 10 via wireless communication. Additionally, in some examples, each impedance measurement of the set of impedance measurements may be conducted for a measurement duration. In some cases, the measurement duration is within a range between 10 seconds and five minutes. In this way, each impedance measurement of the set of impedance measurements may capture several respiration cycles for analysis to determine the respiratory parameter values. Data indicative of the measurement duration may be exported to IMD 10 by external device 12. The data indicative of the measurement duration may be determined based on input to external device 12, such as an input by a clinician.

In some examples, IMD 10 may perform impedance measurements based on a time of day. For example, IMD 10 may perform impedance measurements only during nighttime (e.g., from 12 AM to 6 AM), only during daytime (e.g., from 8 AM to 8 PM), or during all times of the day. In some examples, the impedance measurement rate, the impedance measurement duration, or both, may differ based on the time of day in which IMD 10 performs impedance measurements. IMD 10 may assign timestamps to each impedance measurement, so that impedance data may be analyzed based on the time of day that the data was measured. For example, the impedance data may be analyzed to determine how patient 4's respiratory patterns differ at night (e.g., while patient 4 is sleeping) versus during the day (e.g., while patient 4 is awake).

Components of IMD 10 may be powered by a power source (e.g., a battery). In some examples, the power source may be configured with a limited amount of charge. Impedance measurements may cause components of IMD 10, such as the electrodes, processing circuitry, and sensing circuitry to draw energy (e.g., electrical current) from the power source, thus decreasing the charge of the power source. Any combination of increasing the impedance measurement duration and increasing the impedance measurement rate may cause a rate of energy consumption from the power source to respectively increase. Consequently, it may be beneficial to limit the number and the duration of impedance measurements taken by IMD 10 such that charge is adequately preserved, and enough impedance data is collected to adequately identify or monitor medical conditions based on the impedance data.

Various conditions may affect a quality of impedance data collected by IMD 10 during impedance measurements. For example, if patient 4 is exercising during an impedance measurement, patient 4's respiration rate may be affected (e.g., increased) due to the exercise—and not necessarily due to a medical condition. Additionally, in some cases, patient movements that occur during exercise unrelated to chest cavity movements may introduce noise into impedance data collected by IMD 10. In this way, it may be beneficial for IMD 10 to avoid performing impedance measurements while patient 4 is active or exclude impedance data collected while patient 4 is active from analysis to identify or monitor medical conditions. IMD 10 may include one or more motion sensors. The one or more motion sensors may include an accelerometer that is configured to sense an acceleration of IMD 10. For example, the accelerometer may produce data indicative of acceleration in three directions (e.g., x-axis, y-axis, and z-axis). Based on data produced by the accelerometer, IMD 10 may be configured to determine a motion level, or an "motion count" associated with patient 4.

In some examples, IMD 10 is configured to perform a motion measurement prior to performing an impedance measurement. For example, IMD 10 may determine a motion level associated with patient 4 and compare the motion level with a threshold motion level. If the motion level is greater than or equal to the threshold motion level, IMD 10 may, in some cases, decline to perform the impedance measurement in order to avoid spending energy to obtain data that is potentially compromised due to patient motion. In other cases, if the motion level is greater than or equal to the threshold motion level, IMD 10 may proceed to perform the impedance measurement and mark the data corresponding to the impedance measurement as being performed during high-motion conditions. In this way, the data may be excluded from analysis or an importance of the data during analysis may be decreased.

IMD 10 may measure and analyze other parameters when determining whether to perform an impedance measurement. For example, rather than perform impedance measurements at a measurement rate using IMD 10, in some examples, certain measured parameters may "trigger" IMD 10 to perform an impedance measurement. Such parameters may include heart rate, patient posture, patient motion, ECG, a presence or an absence of one or more arrhythmias, patient triggers, and acoustic data. For example, IMD 10 may perform an impedance measurement in response to a change in patient posture, a change in heart rate, or a detection of a sounds (e.g., snoring) indicative of a medical condition such as sleep apnea.

In some examples, to perform an impedance measurement, IMD 10 collects a set of "primary" impedance values at a sampling rate. In some examples, the set of primary impedance values is collected at a sampling rate within a range between 100 Hertz (Hz) and 300 Hz for a period of time lasting throughout the impedance measurement duration. In one example, the set of primary impedance values is collected at a sampling rate of 128 Hz. In another example, the set of primary impedance values is collected at a sampling rate of 256 Hz. In some examples, each primary impedance value of the set of primary impedance values defines 14-bit resolution. In some examples, IMD 10 truncates the 14-bit resolution to a 12-bit resolution. Such a truncation may be done by first filtering the impedance signal and then preserving the lowest 12-bit resolution to improve a resolution for a small respiration signal which is of the order of 2-3 ohms. After collecting the set of primary impedance values, IMD 10 may process the set of primary impedance values to obtain a set of "secondary" impedance values, where the set of secondary impedance values is smaller than the set of primary impedance values. Such filtering may, in some cases, help processing circuitry 14 to identify respiration parameter values from the impedance data. As used herein, the adjectives "primary" and "secondary" are not intended to indicate an order or a preference between groups but merely to distinguish between groups.

IMD 10 may include, for example, a low-pass filter, a high-pass filter, and a decimator filter. The decimator filter, in some cases, may include a third order cascaded integrator-comb (CIC) decimator. As a part of processing the set of primary impedance values to obtain a set of secondary impedance values, IMD 10 may use the decimator filter to downsample a first set of primary impedance values to obtain a second set of primary impedance values, where the second set of primary impedance values is smaller than the first set of primary impedance values. As an example, IMD 10 may downsample the first set of primary impedance values, which may have a sampling rate of 256 Hz to obtain the second set of primary impedance values, which may have a sampling rate of 8 Hz. In other words, IMD 10 may use the decimator filter select every $32^{nd}$ impedance value of the first set of primary impedance values to generate the second set of primary impedance values. In some examples, IMD 10 may downsample the first set of primary impedance values according to R-waves, e.g., with a sample timing based on the timing of R-waves, detected by IMD 10 in an ECG signal. By downsampling the set of primary impedance values, IMD 10 may decrease a number of impedance values that must pass through the high-pass filter and the low-pass filter, thus decreasing the power consumption of the high-pass filter and the low-pass filter.

After using the decimeter filter to obtain the second set of primary impedance values, IMD 10 may use the high-pass filter and the low-pass filter to filter the second set of primary impedance values to obtain the set of secondary impedance values. In some examples, the low-pass filter of IMD 10 includes a fourth order elliptical filter having a cutoff frequency between 0.50 Hz and 0.75 Hz. For example, the cutoff frequency of the low-pass filter may be 0.65 Hz. In some examples, the high-pass filter may include a first-order filter having a cutoff frequency between 0.02 Hz and 0.10 Hz. For example, the cutoff frequency of the high-pass filter may be 0.04 Hz. In this way, the combination of the high-pass filter and the low-pass filter may effectively form a band-pass filter which attenuates frequencies outside of a frequency band extending between the cutoff frequency of the high-pass filter to the cutoff frequency of the low-pass filter. For example, the low-pass filter may attenuate higher-frequency components of the secondary set of impedance values that are related to cardiac functions of patient 4—helping to extract lower-frequency components from the impedance data that are related to respiratory functions of patient 4. In other words, IMD 10 may extract a respiratory envelope from the impedance data. Additionally, the filters of IMD 10 may, in some cases, attenuate a DC component of the impedance signal.

A settling time of an electrical component (e.g., an electronic filter or an electronic amplifier) may be given by an amount of time elapsed from a beginning of an input to the component to a time in which an output from the component enters and remains within an error band. It may be beneficial to limit a settling time of an electronic filter in order to decrease the amount of time before the electronic filter is able to efficiently produce a reliable output. In some examples, a settling time of the high-pass filter and the low-pass filter of IMD 10 may be less than or equal to 0.5 seconds. In some cases, during an impedance measurement, IMD 10 may discard the first three samples of the set of secondary impedance values output by the high-pass filter and the low-pass filter in order to improve a quality of the secondary impedance values. In some examples, additional settling may take place after the settling time has passed if a peak impedance value occurs during filter initialization.

In some examples, during an impedance measurement performed by IMD 10, the filters (e.g., the high-pass filter, the low-pass filter, and the decimator filter) are activated for a first initialization period which allows the filters to settle before the first set of primary impedance values are recorded. In some examples, the first initialization period is within a range between 50 milliseconds (ms) and 200 ms. For example, the first initialization period may last for 120 ms. During a second initialization period, the decimator filter may, in some cases, accept as an input an initial group of primary impedance values from the first set of primary impedance values, the initial group of primary impedance values fully initializing the decimator filter. In turn, the decimator filter provides an output which may be used to initialize the high-pass filter and the low-pass filter. In some examples, the second initialization period is within a range between 200 ms and 500 ms. For example, the second initialization period may last for 375 ms. IMD 10 may calculate internal filter states for the low-pass filter and the high-pass filter such that they are in a steady state with the output of the decimator filter. In some examples, this is done immediately when the decimator output becomes available. In some examples, IMD 10 may calculate the internal filter states in an amount of time corresponding to a single impedance value. After the first initialization period and the second initialization period, a DC offset may be mostly eliminated from the impedance data.

Although, in some cases, IMD 10 may implement a hardware high-pass filter and a hardware low-pass filter, IMD 10 may alternatively use other filtering methods to process data corresponding to an impedance measurement. For example, IMD 10 may apply a 64-point smoothing filter and subtract an output of the smoothing filter from the original impedance signal to remove DC and linear components of the impedance signal. Subsequently, IMD 10 may filter the impedance data with a low-pass filter having a cutoff frequency of 0.65 Hz. The low-pass filter may, in some cases, implement 50 dB attenuation. In some examples, cutoff frequencies of the hardware high-pass filter and the hardware low-pass filter may be selected in order to pass a respiration pattern within a range between 4 breaths per minute and 24 breaths per minute.

In some examples, after IMD 10 processes the primary impedance values to obtain the set of secondary impedance values, IMD 10 may save the set of secondary impedance values in a storage device. In some examples, IMD 10 may save the set of secondary impedance values in the storage device with a timestamp that identifies a time in which the impedance measurement corresponding to the set of secondary impedance values was taken by IMD 10. In some examples, IMD 10 may output the set of secondary impedance values to another device, such as external device 12 for analysis. In other examples, processing circuitry of IMD 10 may analyze the set of secondary impedance values. In any case, the set of secondary impedance values may be analyzed by processing circuitry (e.g., processing circuitry 14) to determine one or more respiratory parameters (e.g., respiratory rate, respiratory rate variability, and respiratory effort corresponding to the respective impedance measurement.

In some examples, processing circuitry 14 identifies one or more respiration parameters associated with an impedance measurement. For example, processing circuitry 14 may analyze the set of secondary impedance values representing the filtered impedance data collected by IMD 10 during an impedance measurement. The set of secondary impedance values, in some examples, represents a first set of secondary impedance values. To identify the one or more respiration parameters, processing circuitry 14 is configured to calculate, based on the first set of secondary impedance values, a mean secondary impedance value and subtract, from each secondary impedance value of the first set of secondary impedance values, the mean secondary impedance value to obtain a second set of secondary impedance values. In some examples, to produce the second set of secondary impedance values, processing circuitry 14 is configured to perform the following operation:

$$\textit{impedanceSignal} = \text{impedance} - \text{mean(impedance)} \quad \text{(eq. 1)}$$

The term "impedance" may represent the first set of secondary impedance values, the term "mean(impedance)" may represent the mean value of the first set of secondary impedance values, and the term "impedanceSignal" may represent the second set of secondary impedance values.

In some examples, processing circuitry 14 determines the second set of secondary impedance values by calculating a separate mean impedance value corresponding to each impedance value of the first set of secondary impedance values. In some examples, the mean impedance value corresponding to each impedance value of the first set of secondary impedance values represents a moving average of the first set of secondary impedance values. For example, processing circuitry 14 may apply an m-sample moving average, where the respective mean impedance value corresponding to each impedance value represents a mean impedance value of m (e.g., m=64 when first set of impedance values is sampled at 8 Hz) impedance values preceding the respective impedance value. In some cases, to implement the moving average, processing circuitry 14 may apply a high pass filter to the first set of secondary impedance values in order to obtain the second set of secondary impedance values.

Additionally, in some examples, the mean impedance value corresponding to each impedance value of the first set of secondary impedance values represents a weighted moving average of the first set of secondary impedance values. For example, processing circuitry 14 may apply an n-sample weighted moving average, where the respective mean impedance value corresponding to each impedance value represents a weighted mean impedance value of n impedance values preceding the respective impedance value. An example set of weights for the weighted moving average may include [1/64, 1/16−1/32, 1/16, 1/16+1/32, 1/8, 1/8+1/32, 1/8+1/32, 1/8+1/32, 1/8, 1/16+1/32, 1/16, 1/16−1/32, 1/64]. In some cases, to implement the moving average, processing circuitry 14 may apply a low pass filter to the first set of secondary impedance values in order to obtain the second set of secondary impedance values.

By subtracting the mean secondary impedance value from the first set of secondary impedance values to obtain the second set of secondary impedance values, processing circuitry 14 may offset the respiratory waveform represented by the set of secondary impedance values such that the mean secondary impedance value of the second set of secondary impedance values is zero Ohms (Ω). Such an offset may center the respiratory waveform, such that the respiratory waveform oscillates about the y=0 Ω axis.

In some examples, processing circuitry 14 may calculate a derivative of the second set of secondary impedance values to obtain a third set of secondary impedance values. For example, to calculate the derivative, processing circuitry 14 may determine a derivative value corresponding to each secondary impedance value of the second set of secondary impedance values. As described herein, a derivative value may represent a slope, or an approximation of a slope of the impedance signal (i.e., the second set of secondary impedance values) at a respective secondary impedance value of the second set of secondary impedance values. In some examples, to calculate the derivative, processing circuitry 14 performs the following operations:

$$impedanceDifference(n) = 0 \text{ for } n = 1, 2, \text{ and } 3 \quad \text{(eq. 2)}$$

$$impedanceDifference(n) = \text{impedance}(n+1) - \text{impedance}(n-3) \text{ for } n > 3 \quad \text{(eq. 3)}$$

In some cases, "impedanceDifference" may represent the third set of n secondary impedance values. As seen in eq. 2, processing circuitry 14 may set the first three values of the third set of secondary impedance values to zero. Additionally, in some cases, processing circuitry 14 may subtract, for each value n of the third set of secondary impedance values, a first value of the first set of secondary impedance values (i.e., impedance(n−3)) from a second value of the first set of secondary impedance values (i.e., impedance(n+1)). In other words, the first value may correspond to a value of first set of secondary impedance values that occurs three values prior to the respective value n of the third set of secondary impedance values and the second value may correspond to a value of first set of secondary impedance values that occurs one value after the respective value n of the third set of secondary impedance values. As such, the first value and the second value may be separated by three impedance values. Since each pair of consecutive impedance values in the first set of secondary impedance values may be separated by the same time interval, the difference operation may represent an accurate approximation of the derivative. In some examples, the first value and the second value may be separated by greater than three impedance values. In some examples, the first value and the second value may be separated by less than three impedance values.

After processing circuitry 14 determines the third set of secondary impedance values (e.g., the derivative of the second set of secondary impedance values), processing circuitry may identify zero crossings in the second set of secondary impedance values (e.g., the impedance signal centered around the y=0 Ω axis). Zero crossings in the impedance signal may approximately correspond to midpoints or peaks in patient 4's inhale phases and exhale phases. Zero crossings may be further sorted into a group of positive zero crossings and a group of negative zero crossings. In some examples, each positive zero crossing of the group of positive zero crossings represents a point in which the second set of secondary impedance values transitions from a negative value to a positive value. Additionally, in some examples, each negative zero crossing of the group of negative zero crossings represents a point in which the second set of secondary impedance values transitions from a positive value to a negative value.

In some examples, processing circuitry 14 may be configured to identify, based on the second set of secondary impedance values and the third set of secondary impedance values, a group of secondary impedance values representing a group of positive zero crossings. For example, processing circuitry 14 may determine, if the following conditions (e.g., equations 4-8) are met, that a secondary impedance value n of the second set of secondary impedance values represents a positive zero crossing.

$$impedanceSignal(n) \cdot impedanceSignal(n-1) \leq 0 \quad \text{(eq. 4)}$$

$$impedanceSignal(n) > 0 \quad \text{(eq. 5)}$$

$$impedanceDifference(n) > positiveThreshold(n-1) \quad \text{(eq. 6)}$$

$$positiveBlank(n) = 0 \quad \text{(eq. 7)}$$

$$n > 1 \quad \text{(eq. 8)}$$

By multiplying each pair of consecutive secondary impedance values (i.e., impedanceSignal(n) and impedanceSignal(n−1)) of the second set of secondary impedance values as seen in equation 4, processing circuitry 14 may identify each pair of consecutive secondary impedance values where one secondary impedance value is negative and one secondary impedance value is positive. As such, in some examples, processing circuitry 14 may identify every zero crossing in the impedance signal (e.g., every point in the second set of secondary impedance values where the secondary impedance values cross the y=0Ω axis), where each zero crossing is represented by a pair of consecutive secondary impedance values where one secondary impedance value is negative and one secondary impedance value is positive. Additionally, or alternatively, in some examples, to identify a zero crossing event, processing circuitry 14 may identify sign changes in the second set of secondary impedance values. A sign of a particular impedance value may be given by a binary digit (e.g., "1" for positive and "0" for negative). As such, processing circuitry 14 may search for instances in which the binary digit indicative of sign changes from 0 to 1 or changes from 1 to 0.

As seen in equation 5, processing circuitry 14 may determine, for each pair of consecutive secondary impedance values where one secondary impedance value is negative and one secondary impedance value is positive, if a leading secondary impedance value (i.e., impedanceSignal (n)) is greater than zero. Additionally, if a corresponding impedance value of the derivative (i.e., impedanceDifference(n)) is greater than a threshold (positiveThreshold (n−1)), if the respective secondary impedance value n is outside of a blanking window, and if n>1, processing circuitry 14 may determine that the conditions of equations 5-8 are met, and thus determine that secondary impedance value n represents a positive zero crossing.

In some examples, processing circuitry 14 may be configured to identify, based on the second set of secondary impedance values and the third set of secondary impedance values, a group of secondary impedance values representing a group of negative zero crossings. For example, processing circuitry 14 may determine, if the following conditions (e.g., equations 9-13) are met, that a secondary impedance value n of the second set of secondary impedance values represents a negative zero crossing.

$$impedanceSignal(n) \cdot impedanceSignal(n-1) \leq 0 \quad \text{(eq. 9)}$$

$$impedanceSignal(n) < 0 \quad \text{(eq. 10)}$$

$$impedanceDifference(n) > negativeThreshold(n-1) \quad \text{(eq. 11)}$$

$$negativeBlank(n) = 0 \quad \text{(eq. 12)}$$

$$n > 1 \quad \text{(eq. 13)}$$

By multiplying each pair of consecutive secondary impedance values (i.e., impedanceSignal(n) and impedanceSignal(n−1)) of the second set of secondary impedance values as seen in equation 4, processing circuitry 14 may identify each pair of consecutive secondary impedance values where one secondary impedance value is negative and one secondary impedance value is positive. In this way, equation 9 may be the same as equation 4. As such, in some examples, processing circuitry 14 may identify every zero crossing in the impedance signal (e.g., every point in the second set of secondary impedance values where the secondary impedance values cross the y=0Ω axis), where each zero crossing corresponds to a pair of consecutive secondary impedance values where one secondary impedance value is negative and one secondary impedance value is positive. Additionally, or alternatively, in some examples, to identify a zero crossing event, processing circuitry 14 may identify sign changes in the second set of secondary impedance values. A sign of a particular impedance value may be given by a binary digit (e.g., "1" for positive and "0" for negative). As such, processing circuitry 14 may search for instances in which the binary digit indicative of sign changes from 0 to 1 or changes from 1 to 0.

As seen in equation 9, processing circuitry 14 may determine, for each pair of consecutive secondary impedance values where one secondary impedance value is negative and one secondary impedance value is positive, if a leading secondary impedance value (i.e., impedanceSignal (n)) is less than zero. Additionally, if a corresponding impedance value of the derivative (i.e., impedanceDifference(n)) is less than a negative threshold (negativeThreshold (n−1)), if the respective secondary impedance value n is outside of a blanking window, and if n>1, processing circuitry 14 may determine that the conditions of equations 9-13 are met, and thus determine that secondary impedance value n represents a negative zero crossing.

As seen in equation 7 and equation 12, processing circuitry 14 may determine whether a secondary impedance value n of the second set of secondary impedance values (i.e., impedanceSignal) is a positive/negative zero crossing based on whether the secondary impedance value n occurs within a blanking window. More specifically, if a positive zero crossing occurs outside of a positive blanking window, processing circuitry 14 may determine that the positive zero crossing passes the condition of equation 7 and add the positive zero crossing to the group of positive zero crossings. Additionally, if a negative zero crossing occurs outside of a negative blanking window, processing circuitry 14 may determine that the negative zero crossing passes the condition of equation 12 and add the negative zero crossing to the group of negative zero crossings. In other words, processing circuitry 14 may reject a potential positive zero crossing within a positive blanking window following a valid positive zero crossing (e.g., an impedance value which satisfies the conditions of equations 4-8). Additionally, processing circuitry 14 may reject a potential negative zero crossing within a negative blanking window following a valid negative zero crossing (e.g., an impedance value which satisfies the conditions of equations 9-13).

In some examples, to determine if a secondary impedance value n of the second set of secondary impedance values satisfies the condition of equation 7, processing circuitry 14 determines whether a positive zero crossing of the group of positive zero crossings exists within a group of consecutive secondary impedance values immediately preceding the secondary impedance value n, where the group of consecutive secondary impedance values represents the positive blanking window. In some examples, the group of consecutive secondary impedance values includes a number of consecutive secondary impedance values within a range between 5 and 15 (e.g., 10). In some cases, if a positive zero crossing does not exist within the group of consecutive secondary impedance values, processing circuitry 14 may determine that positiveBlank(n)=0 and determine that the condition of equation 7 is satisfied for the secondary impedance value n. Alternatively, if a positive zero crossing does exist within the group of consecutive secondary impedance values, processing circuitry 14 may determine that positiveBlank(n)=1 and determine that the condition of equation 7 is not satisfied for the secondary impedance value n.

In some examples, to determine if a secondary impedance value n of the second set of secondary impedance values satisfies the condition of equation 12, processing circuitry 14 determines whether a negative zero crossing of the group of negative zero crossings exists within a group of consecutive secondary impedance values immediately preceding the secondary impedance value n, where the group of consecutive secondary impedance values represents the negative blanking window. In some examples, the group of consecutive secondary impedance values includes a number of consecutive secondary impedance values within a range between 5 and 15 (e.g., 10). In some cases, if a negative zero crossing does not exist within the group of consecutive secondary impedance values, processing circuitry 14 may determine that negativeBlank(n)=0 and determine that the condition of equation 12 is satisfied for the secondary impedance value n. Alternatively, if a negative zero crossing does exist within the group of consecutive secondary impedance values, processing circuitry 14 may determine that negativeBlank(n)=1 and determine that the condition of equation 12 is not satisfied for the secondary impedance value n.

Processing circuitry 14 may, in some examples, be configured to detect peaks in the third set of secondary impedance values (e.g., the derivative of the impedance signal given by the first set of secondary impedance values. For example, processing circuitry 14 may be configured to detect a set of positive peaks and a set of negative peaks in the third set of secondary impedance values. In some examples, processing circuitry 14 determines the set of positive peaks and a maximum positive peak according to the following equation.

$$positivePeak = impedancedifference(n) * \text{POS\_PEAK\_FRACTION} \quad \text{(eq. 14)}$$

Processing circuitry 14 may identify a positive peak of the set of positive peaks according to equation 14 if the following conditions are met:

$$impedanceDifference(n) = * \text{POS\_PEAK\_FRACTION} > positivePeak \quad \text{(eq. 15)}$$

$$positiveBlank(n) = 1 \quad \text{(eq. 16)}$$

If the conditions of equation 15 and equation 16 are not satisfied, processing circuitry may determine that:

$$positivePeak = 0 \quad \text{(eq. 17)}$$

In other words, processing circuitry 14 may determine if a fraction (e.g., POS_PEAK_FRACTION) of the respective secondary impedance value is greater than a previously-identified positive peak. Additionally, processing circuitry 14 may determine whether the respective secondary impedance value falls within a positive blanking window corresponding to a positive zero crossing. If the fraction of the respective secondary impedance value is greater than the previously-identified positive peak and if the respective secondary impedance value falls within the positive blanking window, processing circuitry 14 may determine that the respective secondary impedance value of the third set of secondary impedance values is a positive peak. In some examples, processing circuitry 14 may identify at most one positive peak corresponding to each positive zero crossing of the group of positive zero crossings. A respective positive peak, in some cases, may be used to determine an initial threshold value (e.g., positiveThreshold) used to identify a subsequent positive zero crossing. In other words, the positive peak determined in equations 14-17 may be used to determine a threshold that is used to evaluate whether a particular secondary impedance value represents a positive zero crossing (e.g., the condition of equation 6). Processing circuitry 14 may determine a maximum positive peak according to the following equations:

$$positivePeak = \text{MAX\_POSITIVE\_PEAK if:} \quad \text{(eq. 18)}$$

$$positivePeak > \text{MAX\_POSITIVE\_PEAK} \quad \text{(eq. 19)}$$

In other words, processing circuitry 14 may identify a positive peak as a maximum positive peak if the positive peak is greater than a previously-identified maximum positive peak.

Additionally, in some examples, processing circuitry 14 is configured to determine the set of negative peaks and a minimum negative peak according to the following equation.

$$negativePeak = impedanceDifferance(n) * \text{NEG\_PEAK\_FRACTION} \quad \text{(eq. 20)}$$

Processing circuitry 14 may identify a negative peak of the set of negative peaks according to equation 20 if the following conditions are met:

$$impedanceDifferance(n) * \text{NEG\_PEAK\_FRACTION} < negativePeak \quad \text{(eq. 21)}$$

$$negativeBlank(n) = 1 \quad \text{(eq. 22)}$$

If the conditions of equation 21 and equation 22 are not satisfied, processing circuitry may determine that:

$$negativePeak = 0 \quad \text{(eq. 23)}$$

In other words, processing circuitry 14 may determine if a fraction (e.g., NEG_PEAK_FRACTION) of the respective secondary impedance value is lower than a previously-identified negative peak. Additionally, processing circuitry 14 may determine whether the respective secondary impedance value falls within a negative blanking window corresponding to a negative zero crossing. If the fraction of the respective secondary impedance value is lower than the previously-identified negative peak and if the respective secondary impedance value falls within the negative blanking window, processing circuitry 14 may determine that the respective secondary impedance value of the third set of secondary impedance values is a negative peak. In some examples, processing circuitry 14 may identify at most one negative peak corresponding to each negative zero crossing of the group of negative zero crossings. A respective negative peak, in some cases, may be used to determine an initial threshold value (e.g., negativeThreshold) used to identify a subsequent negative zero crossing. In other words, the negative peak determined in equations 20-23 may be used to determine a threshold that is used to evaluate whether a particular secondary impedance value represents a negative zero crossing (e.g., the condition of equation 11). Processing circuitry 14 may determine a minimum negative peak according to the following equations:

$$negativePeak = \text{MIN\_NEGATIVE\_PEAK} \quad \text{(eq. 24)}$$

$$negativePeak < \text{MIN\_NEGATIVE\_PEAK} \quad \text{(eq. 25)}$$

In other words, processing circuitry 14 may identify a negative peak as a minimum negative peak if the negative peak is less than a previously-identified minimum negative peak.

In some examples, POS_PEAK_FRACTION is a constant value within a range between 0.5 and 0.9 (e.g., 0.7). Additionally, in some examples, NEG_PEAK_FRACTION is a constant value within a range between 0.5 and 0.9 (e.g., 0.7).

As seen in equation 6 and equation 11, when determining whether a respective secondary impedance value n of the second set of secondary impedance values represents a positive zero crossings or a negative zero crossing, processing circuitry 14 may be configured to compare a secondary impedance value n of the third set of secondary impedance values with a positive threshold or a negative threshold, respectively. The secondary impedance value n of the third set of secondary impedance values may, in some cases, be associated with the respective secondary impedance value n of the second set of secondary impedance values. In some examples, processing circuitry 14 adjusts the positive threshold throughout the third set of secondary impedance values according to the following equations.

$$positiveThreshold\ (n = 1) = \text{POSITIVE\_FLOOR} \quad \text{(eq. 26)}$$

$$positiveThreshold\ (n) = positivePeak \quad \text{(eq. 27)}$$

$$\text{if the following condition is met: } positiveBlank(n) = 1 \quad \text{(eq. 28)}$$

Alternatively, in some examples, processing circuitry 14 determines the positive threshold according to the following equations.

$$positiveThreshold(n) = positiveThreshold(n-1) - \text{POSITIVE\_SLOPE} \quad \text{(eq. 29)}$$

$$positiveBlank(n) = 0; \text{ and} \quad \text{(eq. 30)}$$

$$n > 1 \quad \text{(eq. 31)}$$

If processing circuitry 14 determines the positive threshold to be below the positive floor, processing circuitry 14 may reset the positive threshold to the positive floor.

$$\text{positive Threshold } (n) = \text{POSITIVE\_FLOOR} \quad \text{(eq. 32)}$$

$$\text{if the following condition is met: } positiveThreshold\,(n) < \text{POSITIVE\_FLOOR} \quad \text{(eq. 33)}$$

In some examples, processing circuitry 14 adjusts the negative threshold throughout the third set of secondary impedance values according to the following equations.

$$negativeThreshold(n = 1) = \text{NEGATIVE\_FLOOR} \quad \text{(eq. 34)}$$

$$negativeThreshold(n) = negativepeak \quad \text{(eq. 35)}$$

$$neagativeBlank(n) = 1 \quad \text{(eq. 36)}$$

Alternatively, in some examples, processing circuitry 14 determines the negative threshold according to the following equations.

$$negativeThreshold(n) = neagativeThreshold(n-1) + \text{NEGATIVE\_SLOPE} \quad \text{(eq. 37)}$$

$$\text{the following condition is met:} neagativeBlank(n) = 0 \quad \text{(eq. 38)}$$

If processing circuitry 14 determines the negative threshold to be above the negative floor, processing circuitry 14 may reset the negative threshold to the negative floor.

$$negativeThreshold(n) = \text{NEGATIVE\_FLOOR if the following condition is met:} \quad \text{(eq. 39)}$$

$$negativeThreshold(n) > \text{NEGATIVE\_FLOOR} \quad \text{(eq. 40)}$$

In some examples, POSITIVE_FLOOR=0.1, NEGATIVE_FLOOR=−0.1, POSITIVE_SLOPE=0.01, and NEGATIVE_SLOPE=−0.01.

In some examples, after processing circuitry 14 identifies the group of negative zero crossings and the group of positive zero crossings, processing circuitry 14 is configured to determine, based on the group of negative zero crossings, a first set of respiration intervals. Each respiration interval of the first set of respiration intervals may indicate an amount of time separating each pair of consecutive negative zero crossings of the group of negative zero crossings. Additionally, processing circuitry 14 may determine, based on the group of positive zero crossings, a second set of respiration intervals. Each respiration interval of the second set of respiration intervals may represent an amount of time separating each pair of consecutive positive zero crossings of the group of positive zero crossings. In this way, processing circuitry 14 is configured to determine an amount of time that patient 4 takes to perform each complete respiration cycle occurring during the impedance measurement corresponding to the impedance data (e.g., the first set of secondary impedance values). By determining the respiration intervals based on both of the positive zero crossings and the negative zero crossings, processing circuitry 14 may, in some cases, increase a number of respiration intervals for analysis (versus determining the respiration intervals based on only the positive zero crossings or versus determining the respiration intervals based on only the negative zero crossings).

In some examples, the first set of respiration intervals may be negative zero-crossing intervals ($N_i$) each defining a time difference between consecutive negative zero-crossings. Additionally, in some examples, the second set of respiration intervals may be positive zero-crossing intervals ($P_i$) each defining a time difference between consecutive positive zero crossings. In some examples, processing circuitry 14 determines that an impedance measurement is valid if a number of positive zero-crossing intervals is greater than zero, a number of negative zero-crossing intervals is greater than zero, or if both the number of positive zero-crossing intervals and the number of negative zero-crossing intervals are greater than zero. In some examples, processing circuitry 14 may determine a respiration interval associated with a respective impedance measurement based on the following principals.

$$\text{If count}(P_i) > 0 \text{ and count}(N_i) = 0, \text{ then } respirationInterval = \text{median}(P_i)$$

$$\text{If count}(P_i) = 0 \text{ and count }(N_i) > 0, \text{ then respirationInterval} = \text{median}(N_i)$$

$$\text{If count}(P_i) > 0 \text{ and count }(N_i) > 0, \text{ then } respirationInterval = \text{median}(P_i, N_i)$$

Additionally, in some examples where count ($P_i$)>0 and count ($N_i$)>0, processing circuitry 14 may be configured to calculate respiration interval variation according to the following equations.

$$\text{Positive Interval Variation} = \text{count}\left(P_i - \text{median}(P_i) \geq \frac{\text{median}(P_i)}{4}\right)$$

$$\text{Negative Interval Variation} = \text{count}\left(N_i - \text{median}(N_i) \geq \frac{\text{median}(N_i)}{4}\right)$$

In some examples where count($P_i$)>0 and count($N_i$)>0, and where positive interval variation is equal to zero and negative interval variation is greater than zero, processing circuitry 14 may determine that the respiration interval length corresponding to an impedance measurement is a median positive zero-crossing interval. In some examples where count($P_i$)>0 and count($N_i$)>0, and where negative interval variation is equal to zero and positive interval variation is greater than zero, processing circuitry 14 may determine that the respiration interval length corresponding to an impedance measurement is a median negative zero-crossing interval.

As discussed above, processing circuitry 14 is configured to calculate, for each impedance measurement of the set of impedance measurements performed by IMD 10, a group of positive peaks and a group of negative peaks. Processing circuitry 14 may be configured to calculate a mean negative peak of the group of negative peaks and calculate a mean positive peak value of the group of positive peaks. Subsequently, processing circuitry 14 is configured to determine a peak-to-peak value representing a difference between the mean positive peak value and the mean negative peak value.

In some examples, processing circuitry 14 is configured to discriminate between different types of waveforms based on e.g. impedance signal quality (e.g. an amount of artifacts or noise) or types of breathing (e.g. normal breathing, Cheyne-Stokes breathing, and apnea). In some examples, processing circuitry 14 is configured to classify an impedance waveform (e.g., the first set of secondary impedance values corresponding to a respective impedance measurement) as "regular breathing" (e.g., eupnea), or classify the impedance waveform as "non-regular breathing" (e.g. sleep-disordered breathing or Cheyne-Stokes breathing). For data corresponding to each impedance measurement of the set of impedance measurements performed by IMD 10, a set of features may be calculated. In some examples, most of the set of features are calculated as part of the process for determining positive zero crossings and negative zero crossings. In some examples, processing circuitry 14 may build a decision tree based on the set of features. In some cases, the set of features includes the peak-to-peak amplitude of the respiration waveform and a patient motion level.

For processing circuitry 14 to determine that an impedance measurement is valid for determining respiration parameters, in some cases, the peak-to-peak amplitude of the respiration waveform must be greater than a peak-to-peak threshold. In some examples, the peak-to-peak threshold is within a range between 0.4 ohms and 1 ohm (e.g., 0.6 ohms). In some examples, IMD 10 determines whether to perform impedance measurements based on patient motion level. The patient motion level may be given by a motion count determined based on accelerometer data. If the motion level is below a threshold motion level, IMD 10 may perform the impedance measurement. Alternatively, in some cases, IMD 10 performs the impedance measurement if the motion level is below the threshold motion level, but marks the data produced by the impedance measurement as insufficient for respiration trend analysis. In some examples, the threshold motion level is represented by a motion count within a range between 20 and 60 (e.g., 45).

In some examples, the set of features may include a periodicity ("PER") of the impedance waveform. Periodicity may be used to determine whether an impedance measurement is good or bad. Periodicity may enable processing circuitry to account for shallow yet periodic breathing. To compute periodicity, processing circuitry 14 may compute a variability of the set of respiration intervals detected in the respiration waveforms, and determine how many respiration intervals of the set of respiration intervals are within a window surrounding the respiration interval median. In some examples, processing circuitry 14 may determine a median duration of a set of respiration intervals comprising the set of respiration intervals derived from positive zero crossings and the set of respiration intervals derived from negative zero crossings. Subsequently, processing circuitry 14 may determine a respiration interval duration window and determine a number of respiration intervals of the set of respiration intervals which define a duration outside of the respiration interval duration window. Additionally, processing circuitry 14 may determine whether the number of respiration intervals satisfies a threshold number of respiration intervals and determine whether to accept the respective impedance measurement based on the determination of whether the number of respiration intervals satisfies the threshold number of respiration intervals. In some examples, to compute periodicity, processing circuitry 14 may determine a power spectrum of the respiration waveform and determine the periodicity based on the power spectrum.

Additionally, processing circuitry 14 may be configured to determine if a particular peak is a valid peak. For example, if a positive peak or a negative peak meets a positive threshold and a negative threshold, respectively, then the peak may be determined to be a valid peak. Additionally, if a positive peak or a negative peak does not meet a positive threshold and a negative threshold, respectively, then the peak may be determined to be an invalid peak. Additionally, in some examples, if ImpedanceSignal in Equation 1 is greater than or less than a threshold value, the impedance may be rejected as a noisy segment.

In some examples, processing circuitry 14 may be configured to calculate, based on the first set of respiration intervals associated with the group of negative zero crossings and the second set of respiration intervals associated with the group of positive zero crossings, a respiration rate associated with a respective impedance measurement. In some examples, to calculate the respiration rate, processing circuitry 14 is configured to combine the first set of respiration intervals and the second set of respiration intervals into a third set of respiration intervals, determine a median respiration interval of the third set of respiration intervals, and calculate, based on the median respiration interval, the respiration rate associated with the respective impedance measurement.

A respiration rate, in some examples, may be computed based on a median respiration rate over a predetermined period. For example, processing circuitry 14 may calculate a daily respiration rate based on all valid impedance measurements taken on the respective day, a daytime respiration rate using all valid impedance measurements taken between, for example, 7 AM and 11 PM, and a nighttime respiration rate based on all valid impedance measurements taken between, for example, 12 AM and 6 AM. Additionally, in some examples, respiration rate may be computed while patient 4 is at rest or while patient 4 rest following a period of exercise. In some examples, the Respiration Rate is equal to 60*8/(Median Respiration cycle lengths in number of samples during valid impedance segments) breaths per minute for raw impedance measurements stored at 8 Hz.

Figure 2:
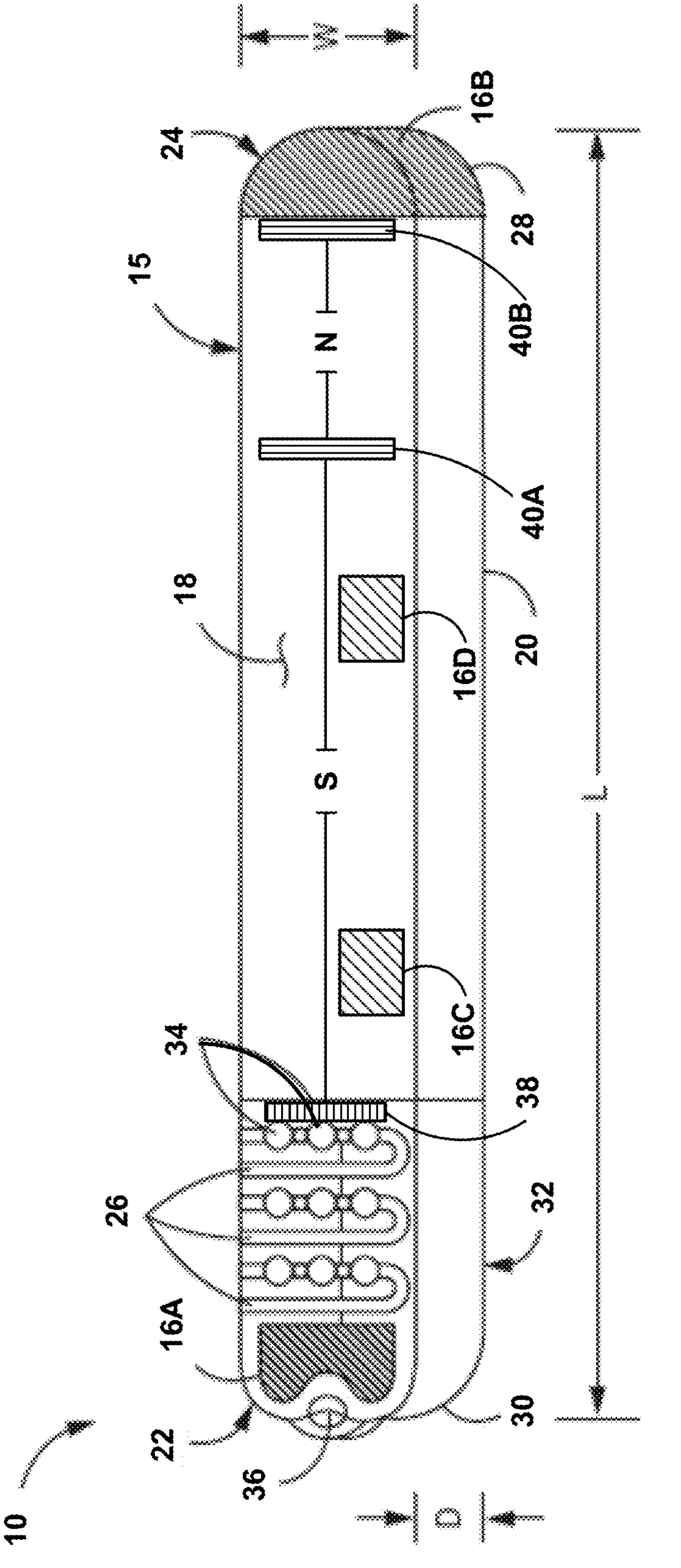
FIG. 2 is a conceptual drawing illustrating an example configuration of the implantable medical device (IMD) of the medical device system of FIG. 1, in accordance with one or more techniques described herein.

FIG. 2 is a conceptual drawing illustrating an example configuration of IMD 10 of the medical device system 2 of FIG. 1, in accordance with one or more techniques described herein. In the example shown in FIG. 2, IMD 10 may include a leadless, subcutaneously-implantable monitoring device having housing 15, proximal electrode 16A, and distal electrode 16B. Housing 15 may further include first major surface 18, second major surface 20, proximal end 22, and distal end 24. In some examples, IMD 10 may include one or more additional electrodes 16C, 16D positioned on one or both of major surfaces 18, 20 of IMD 10. Housing 15 encloses electronic circuitry located inside the IMD 10, and protects the circuitry contained therein from fluids such as body fluids. In some examples, electrical feedthroughs provide electrical connection of electrodes 16A-16D, and antenna 26, to circuitry within housing 15. In some examples, electrode 16B may be formed from an uninsulated portion of conductive housing 15.

In the example shown in FIG. 2, IMD 10 is defined by a length L, a width W, and thickness or depth D. In this example, IMD 10 is in the form of an elongated rectangular prism in which length L is significantly greater than width W, and in which width W is greater than depth D. However, other configurations of IMD 10 are contemplated, such as those in which the relative proportions of length L, width W, and depth D vary from those described and shown in FIG. 2. In some examples, the geometry of the IMD 10, such as the width W being greater than the depth D, may be selected to allow IMD 10 to be inserted under the skin of the patient using a minimally invasive procedure and to remain in the desired orientation during insertion. In addition, IMD 10 may include radial asymmetries (e.g., the rectangular shape) along a longitudinal axis of IMD 10, which may help maintain the device in a desired orientation following implantation.

In some examples, a spacing between proximal electrode 16A and distal electrode 16B may range from about 30-55 mm, about 35-55 mm, or about 40-55 mm, or more generally from about 25-60 mm. Overall, IMD 10 may have a length L of about 20-30 mm, about 40-60 mm, or about 45-60 mm. In some examples, the width W of major surface 18 may range from about 3-10 mm, and may be any single width or range of widths between about 3-10 mm. In some examples, a depth D of IMD 10 may range from about 2-9 mm. In other examples, the depth D of IMD 10 may range from about 2-5 mm, and may be any single or range of depths from about 2-9 mm. In any such examples, IMD 10 is sufficiently compact to be implanted within the subcutaneous space of patient 4 in the region of a pectoral muscle.

IMD 10, according to an example of the present disclosure, may have a geometry and size designed for ease of implant and patient comfort. Examples of IMD 10 described in this disclosure may have a volume of 3 cubic centimeters ($cm^3$) or less, 1.5 $cm^3$ or less, or any volume therebetween. In addition, in the example shown in FIG. 2, proximal end 22 and distal end 24 are rounded to reduce discomfort and irritation to surrounding tissue once implanted under the skin of patient 4. In some examples, a configuration of IMD 10, including instrument and method for inserting IMD 10 is described, for example, in U.S. Patent Publication No. 2014/0276928, incorporated herein by reference in its entirety. In some examples, a configuration of IMD 10 is described, for example, in U.S. Patent Publication No. 2016/0310031, incorporated herein by reference in its entirety.

In the example shown in FIG. 2, first major surface 18 of IMD 10 faces outward towards the skin, when IMD 10 is inserted within patient 4, whereas second major surface 20 is faces inward toward musculature of patient 4. Thus, first and second major surfaces 18, 20 may face in directions along a sagittal axis of patient 4 (see FIG. 1), and this orientation may be maintained upon implantation due to the dimensions of IMD 10.

Proximal electrode 16A and distal electrode 16B may be used to sense cardiac EGM signals (e.g., ECG signals) when IMD 10 is implanted subcutaneously in patient 4. In some examples, processing circuitry of IMD 10 also may determine whether cardiac ECG signals of patient 4 are indicative of arrhythmia or other abnormalities, which processing circuitry of IMD 10 may evaluate in determining whether a medical condition (e.g., heart failure, sleep apnea, or COPD) of patient 4 has changed. The cardiac ECG signals may be stored in a memory of the IMD 10, and data derived from the cardiac ECG signals may be transmitted via integrated antenna 26 to another medical device, such as external device 12. In some examples, one or both of electrodes 16A and 16B also may be used by IMD 10 to detect impedance values during impedance measurements performed by IMD 10. In some examples, such impedance values detected by IMD 10 may reflect a resistance value associated with a contact between electrodes 16A, 16B, and target tissue of patient 4. Additionally, in some examples, electrodes 16A, 16B may be used by communication circuitry of IMD 10 for tissue conductance communication (TCC) communication with external device 12 or another device.

In the example shown in FIG. 2, proximal electrode 16A is in close proximity to proximal end 22, and distal electrode 16B is in close proximity to distal end 24 of IMD 10. In this example, distal electrode 16B is not limited to a flattened, outward facing surface, but may extend from first major surface 18, around rounded edges 28 or end surface 30, and onto the second major surface 20 in a three-dimensional curved configuration. As illustrated, proximal electrode 16A is located on first major surface 18 and is substantially flat and outward facing. However, in other examples not shown here, proximal electrode 16A and distal electrode 16B both may be configured like proximal electrode 16A shown in FIG. 2, or both may be configured like distal electrode 16B shown in FIG. 2. In some examples, additional electrodes 16C and 16D may be positioned on one or both of first major surface 18 and second major surface 20, such that a total of four electrodes are included on IMD 10. Any of electrodes 16A-16D may be formed of a biocompatible conductive material. For example, any of electrodes 16A-16D may be formed from any of stainless steel, titanium, platinum, iridium, or alloys thereof. In addition, electrodes of IMD 10 may be coated with a material such as titanium nitride or fractal titanium nitride, although other suitable materials and coatings for such electrodes may be used.

In the example shown in FIG. 2, proximal end 22 of IMD 10 includes header assembly 32 having one or more of proximal electrode 16A, integrated antenna 26, anti-migration projections 34, and suture hole 36. Integrated antenna 26 is located on the same major surface (e.g., first major surface 18) as proximal electrode 16A, and may be an integral part of header assembly 32. In other examples, integrated antenna 26 may be formed on the major surface opposite from proximal electrode 16A, or, in still other examples, may be incorporated within housing 15 of IMD 10. Antenna 26 may be configured to transmit or receive electromagnetic signals for communication. For example, antenna 26 may be configured to transmit to or receive signals from a programmer via inductive coupling, electromagnetic coupling, tissue conductance, Near Field Communication (NFC), Radio Frequency Identification (RFID), Bluetooth, WiFi, or other proprietary or non-proprietary wireless telemetry communication schemes. Antenna 26 may be coupled to communication circuitry of IMD 10, which may drive antenna 26 to transmit signals to external device 12, and may transmit signals received from external device 12 to processing circuitry of IMD 10 via communication circuitry.

IMD 10 may include several features for retaining IMD 10 in position once subcutaneously implanted in patient 4. For example, as shown in FIG. 2, housing 15 may include anti-migration projections 34 positioned adjacent integrated antenna 26. Anti-migration projections 34 may include a plurality of bumps or protrusions extending away from first major surface 18, and may help prevent longitudinal movement of IMD 10 after implantation in patient 4. In other examples, anti-migration projections 34 may be located on the opposite major surface as proximal electrode 16A and/or integrated antenna 26. In addition, in the example shown in FIG. 2 header assembly 32 includes suture hole 36, which provides another means of securing IMD 10 to the patient to prevent movement following insertion. In the example shown, suture hole 36 is located adjacent to proximal electrode 16A. In some examples, header assembly 32 may include a molded header assembly made from a polymeric or plastic material, which may be integrated or separable from the main portion of IMD 10.

Electrodes 16A and 16B may be used to sense cardiac ECG signals, as described above. Additional electrodes 16C and 16D may be used to sense subcutaneous tissue impedance, in addition to or instead of electrodes 16A, 16B, in some examples. In some examples, processing circuitry of IMD 10 may determine an impedance value of patient 4 based on signals received from at least two of electrodes 16A-16D. For example, processing circuitry of IMD 10 may generate one of a current or voltage signal, deliver the signal via a selected two or more of electrodes 16A-16D, and measure the resulting other of current or voltage. Processing circuitry of IMD 10 may determine an impedance value based on the delivered current or voltage and the measured voltage or current.

In the example shown in FIG. 2, IMD 10 includes a light emitter 38, a proximal light detector 40A, and a distal light detector 40B positioned on housing 15 of IMD 10. Light detector 40A may be positioned at a distance S from light emitter 38, and a distal light detector 40B positioned at a distance S+N from light emitter 38. In other examples, IMD 10 may include only one of light detectors 40A, 40B, or may include additional light emitters and/or additional light detectors. Collectively, light emitter 38 and light detectors 40A, 40B may include an optical sensor, which may be used by IMD 10 to determine, for example, tissue oxygen saturation ($StO_2$) in target tissue of patient 4. Although light emitter 38 and light detectors 40A, 40B are described herein as being positioned on housing 15 of IMD 10, in other examples, one or more of light emitter 38 and light detectors 40A, 40B may be positioned, on a housing of another type of IMD within patient 4, such as a transvenous, subcutaneous, or extravascular pacemaker or ICD, or connected to such a device via a lead. Light emitter 38 includes a light source, such as an LED, that may emit light at one or more wavelengths within the (VIS) and/or (NIR) spectra. For example, light emitter 38 may emit light at one or more of about 660 (nm), 720 nm, 760 nm, 800 nm, or at any other suitable wavelengths.

As shown in FIG. 2, light emitter 38 may be positioned on header assembly 32, although, in other examples, one or both of light detectors 40A, 40B may additionally or alternatively be positioned on header assembly 32. In some examples, light emitter 38 may be positioned on a medial section of IMD 10, such as part way between proximal end 22 and distal end 24. Although light emitter 38 and light detectors 40A, 40B are illustrated as being positioned on first major surface 18, light emitter 38 and light detectors 40A, 40B alternatively may be positioned on second major surface 20. In some examples, IMD may be implanted such that light emitter 38 and light detectors 40A, 40B face inward when IMD 10 is implanted, toward the muscle of patient 4, which may help minimize interference from background light coming from outside the body of patient 4. Light detectors 40A, 40B may include a glass or sapphire window, such as described below with respect to FIG. 4B, or may be positioned beneath a portion of housing 15 of IMD 10 that is made of glass or sapphire, or otherwise transparent or translucent.

In some examples, IMD 10 may include one or more additional sensors, such as one or more accelerometers (not shown). Such accelerometers may be 3D accelerometers configured to generate signals indicative of one or more types of movement of the patient, such as gross body movement (e.g., motion) of the patient, patient posture, movements associated with the beating of the heart, or coughing, rales, or other respiration abnormalities. One or more of the parameters monitored by IMD 10 (i.e., impedance, $StO_2$, or ECG) may fluctuate in response to changes in one or more such types of movement. For example, changes in parameter values sometimes may be attributable to increased patient motion (e.g., exercise or other physical motion as compared to immobility) or to changes in patient posture, and not necessarily to changes in a medical condition. Thus, in some methods of identifying or tracking a medical condition of patient 4, it may be advantageous to account for such fluctuations when determining whether a change in a parameter is indicative of a change in a medical condition.

Figure 3:
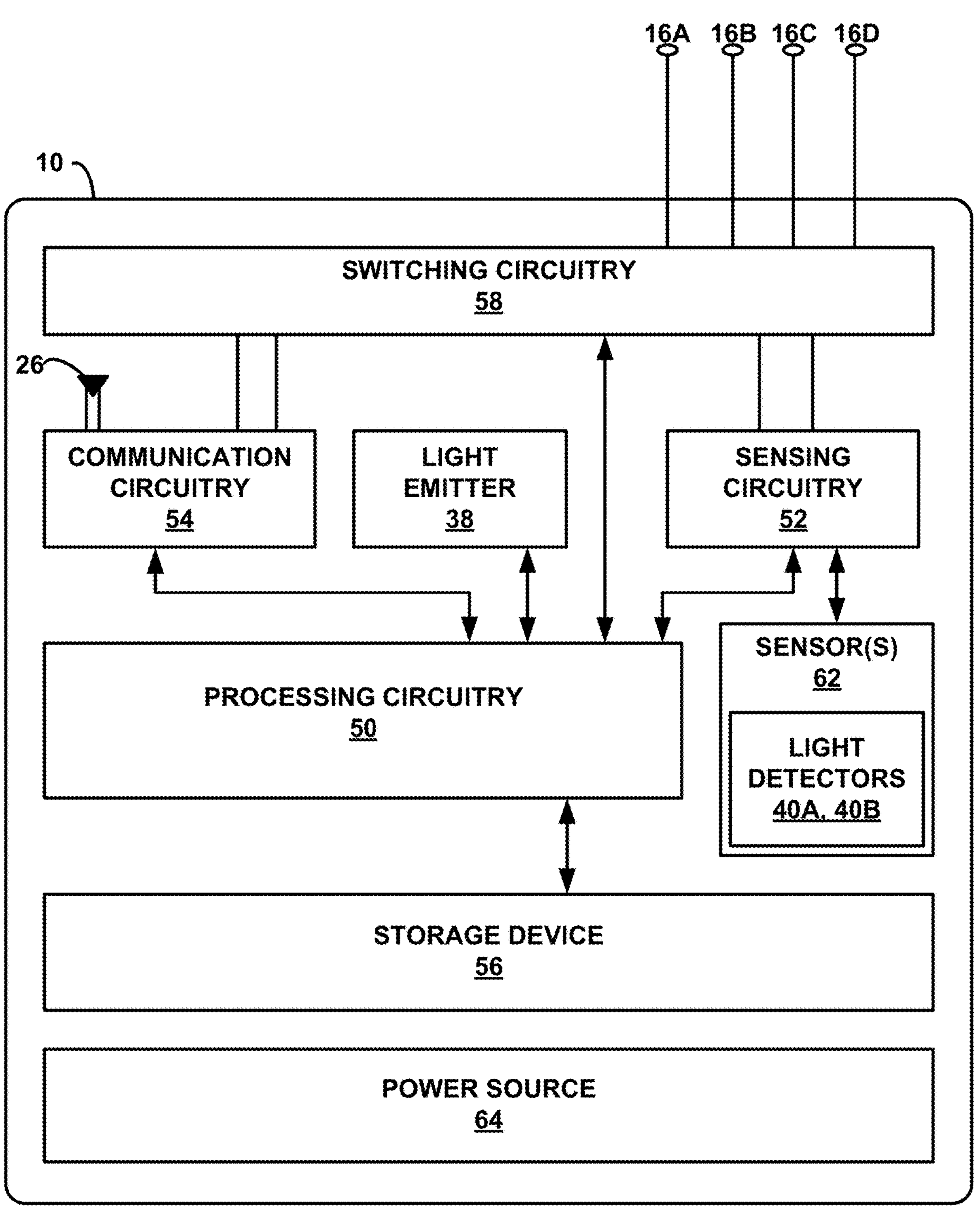
FIG. 3 is a functional block diagram illustrating an example configuration of the IMD of FIGS. 1 and 2, in accordance with one or more techniques described herein.

FIG. 3 is a functional block diagram illustrating an example configuration of IMD 10 of FIGS. 1 and 2, in accordance with one or more techniques described herein. In the illustrated example, IMD 10 includes electrodes 16, antenna 26, light emitter 38, processing circuitry 50, sensing circuitry 52, communication circuitry 54, storage device 56, switching circuitry 58, sensors 62 including light detectors 40, and power source 64.

Processing circuitry 50 may include fixed function circuitry and/or programmable processing circuitry. Processing circuitry 50 may include any one or more of a microprocessor, a controller, a DSP, an ASIC, an FPGA, or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 and communication circuitry 54 may be selectively coupled to electrodes 16A-16D via switching circuitry 58, as controlled by processing circuitry 50. Sensing circuitry 52 may monitor signals from electrodes 16A-16D in order to monitor electrical activity of heart (e.g., to produce an ECG), and/or subcutaneous tissue impedance, the impedance being indicative of at least some aspects of patient 4's respiratory patterns. Sensing circuitry 52 also may monitor signals from sensors 62, which may include light detectors 40A, 40B, and any additional light detectors that may be positioned on IMD 10. In some examples, sensing circuitry 52 may include one or more filters and amplifiers for filtering and amplifying signals received from one or more of electrodes 16A-16D and/or light detectors 40A, 40B.

Communication circuitry 54 may include any suitable hardware, firmware, software or any combination thereof for communicating with another device, such as external device 12 or another IMD or sensor, such as a pressure sensing device. Under the control of processing circuitry 50, communication circuitry 54 may receive downlink telemetry from, as well as send uplink telemetry to, external device 12 or another device with the aid of an internal or external antenna, e.g., antenna 26. In addition, processing circuitry 50 may communicate with a networked computing device via an external device (e.g., external device 12) and a computer network, such as the Medtronic CareLink® Network developed by Medtronic, plc, of Dublin, Ireland.

A clinician or other user may retrieve data from IMD 10 using external device 12, or by using another local or networked computing device configured to communicate with processing circuitry 50 via communication circuitry 54. The clinician may also program parameters of IMD 10 using external device 12 or another local or networked computing device.

In some examples, storage device 56 includes computer-readable instructions that, when executed by processing circuitry 50, cause IMD 10 and processing circuitry 50 to perform various functions attributed to IMD 10 and processing circuitry 50 herein. Storage device 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Power source 64 is configured to deliver operating power to the components of IMD 10. Power source 64 may include a battery and a power generation circuit to produce the operating power. In some examples, the battery is rechargeable to allow extended operation. In some examples, recharging is accomplished through proximal inductive interaction between an external charger and an inductive charging coil within external device 12. Power source 64 may include any one or more of a plurality of different battery types, such as nickel cadmium batteries and lithium ion batteries. A non-rechargeable battery may be selected to last for several years, while a rechargeable battery may be inductively charged from an external device, e.g., on a daily or weekly basis.

Figure 4A:
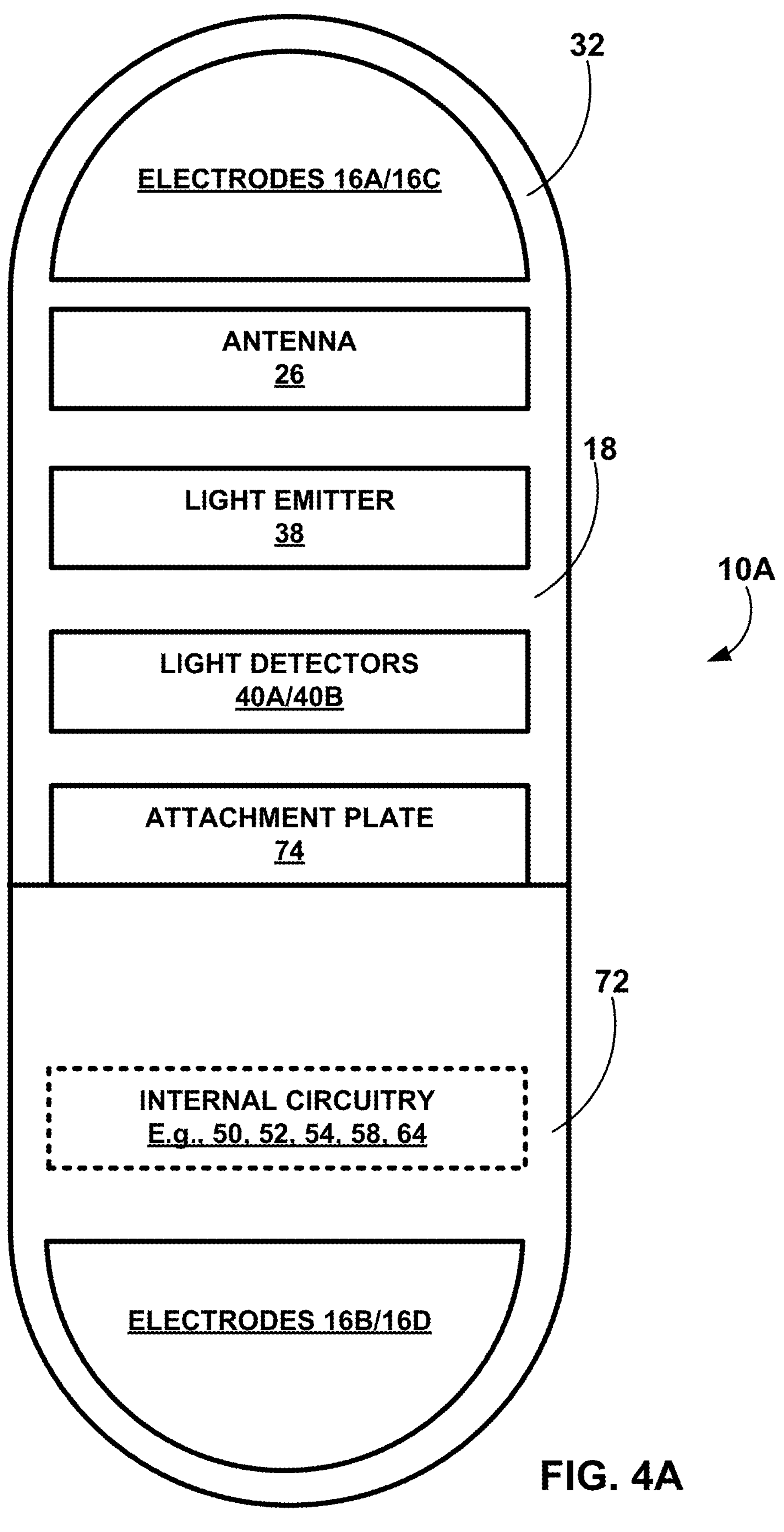
FIGS. 4A and 4B are block diagrams illustrating two additional example IMDs that may be substantially similar to the IMD of FIGS. 1-3, but which may include one or more additional features, in accordance with one or more techniques described herein.
Figure 4B:
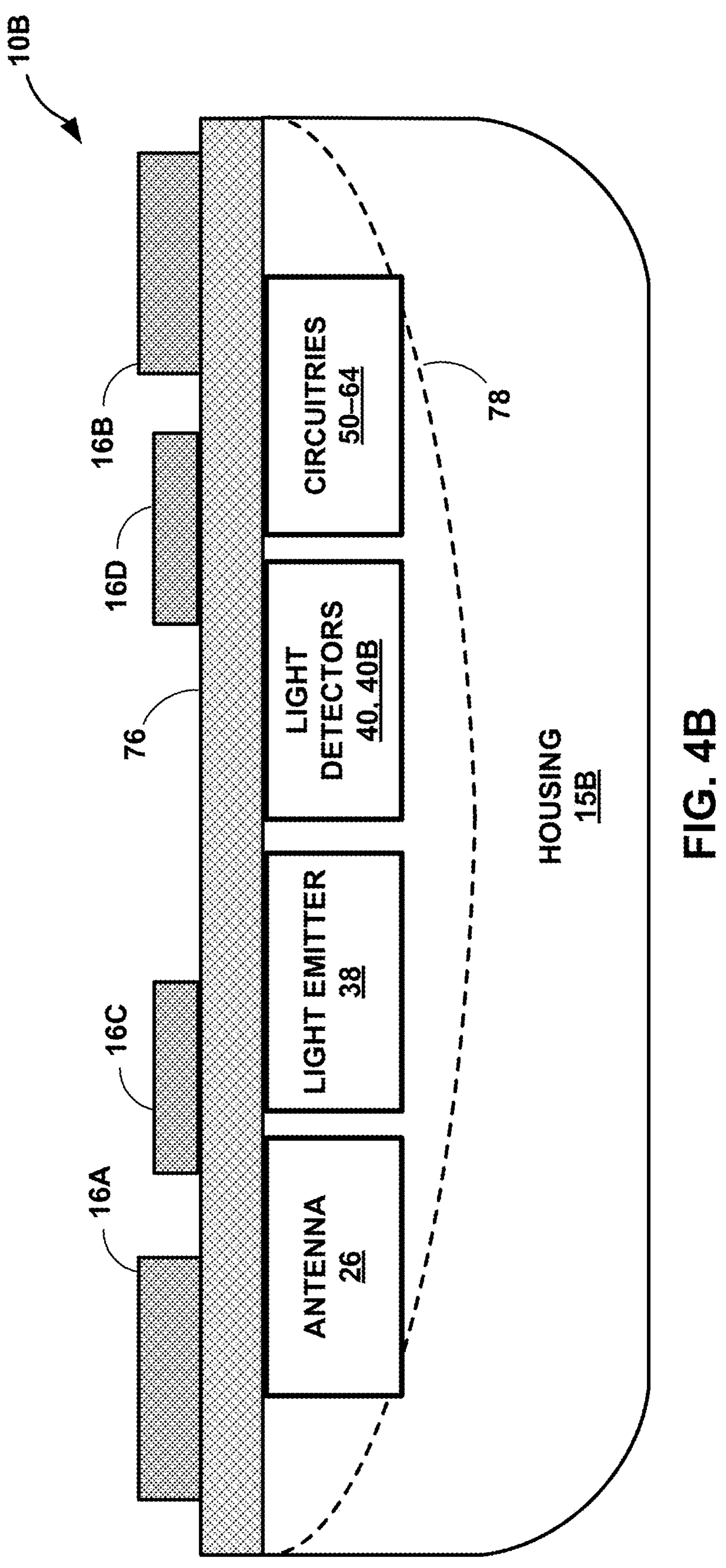

FIGS. 4A and 4B illustrate two additional example IMDs that may be substantially similar to IMD 10 of FIGS. 1-3, but which may include one or more additional features, in accordance with one or more techniques described herein. The components of FIGS. 4A and 4B may not necessarily be drawn to scale, but instead may be enlarged to show detail. FIG. 4A is a block diagram of a top view of an example configuration of an IMD 10A. FIG. 4B is a block diagram of a side view of example IMD 10B, which may include an insulative layer as described below.

FIG. 4A is a conceptual drawing illustrating another example IMD 10A that may be substantially similar to IMD 10 of FIG. 1. In addition to the components illustrated in FIGS. 1-3, the example of IMD 10 illustrated in FIG. 4A also may include a body portion 72 and an attachment plate 74. Attachment plate 74 may be configured to mechanically couple header assembly 32 to body portion 72 of IMD 10A. Body portion 72 of IMD 10A may be configured to house one or more of the internal components of IMD 10 illustrated in FIG. 3, such as one or more of processing circuitry 50, sensing circuitry 52, communication circuitry 54, storage device 56, switching circuitry 58, internal components of sensors 62, and power source 64. In some examples, body portion 72 may be formed of one or more of titanium, ceramic, or any other suitable biocompatible materials.

FIG. 4B is a conceptual drawing illustrating another example IMD 10B that may include components substantially similar to IMD 10 of FIG. 1. In addition to the components illustrated in FIGS. 1-3, the example of IMD 10B illustrated in FIG. 4B also may include a wafer-scale insulative cover 76, which may help insulate electrical signals passing between electrodes 16A-16D and/or optical detectors 40A, 40B on housing 15B and processing circuitry 50. In some examples, insulative cover 76 may be positioned over an open housing 15 to form the housing for the components of IMD 10B. One or more components of IMD 10B (e.g., antenna 26, light emitter 38, light detectors 40A, 40B, processing circuitry 50, sensing circuitry 52, communication circuitry 54, switching circuitry 58, and/or power source 64) may be formed on a bottom side of insulative cover 76, such as by using flip-chip technology. Insulative cover 76 may be flipped onto a housing 15B. When flipped and placed onto housing 15B, the components of IMD 10B formed on the bottom side of insulative cover 76 may be positioned in a gap 78 defined by housing 15B.

Insulative cover 76 may be configured so as not to interfere with the operation of IMD 10B. For example, one or more of electrodes 16A-16D may be formed or placed above or on top of insulative cover 76, and electrically connected to switching circuitry 58 through one or more vias (not shown) formed through insulative cover 76. In addition, to enable IMD 10 to make use of the optical sensor to measure parameters such as $StO_2$, at least a portion of insulative cover 76 may transparent to the NIR or visible wavelengths emitted by light emitter 38 and detected by light detectors 40A, 40B, which in some examples may be positioned on a bottom side of insulative cover 76 as described above.

In some examples, light emitter 38 may include an optical filter between light emitter 38 and insulative cover 76, which may limit the spectrum of emitted light to be within a narrow band. Similarly, light detectors 40A, 40B may include optical filters between light detectors 40A, 40B and insulative cover 76, so that light detectors 40A, 40B detects light from a narrow spectrum, generally at longer wavelengths than the emitted spectrum. Other optical elements that may be included in the IMD 10B may include index matching layers, antireflective coatings, or optical barriers, which may be configured to block light emitted sideways by the light emitter 38 from reaching light detector 40.

Insulative cover 76 may be formed of sapphire (i.e., corundum), glass, parylene, and/or any other suitable insulating material. Sapphire may be greater than 80% transmissive for wavelengths in the range of about 300 nm to about 4000 nm, and may have a relatively flat profile. In the case of variation, different transmissions at different wavelengths may be compensated for, such as by using a ratiometric approach. In some examples, insulative cover 76 may have a thickness of about 300 micrometers to about 600 micrometers. Housing 15B may be formed from titanium or any other suitable material (e.g., a biocompatible material), and may have a thickness of about 200 micrometers to about 500 micrometers. These materials and dimensions are examples only, and other materials and other thicknesses are possible for devices of this disclosure.

Figure 5:
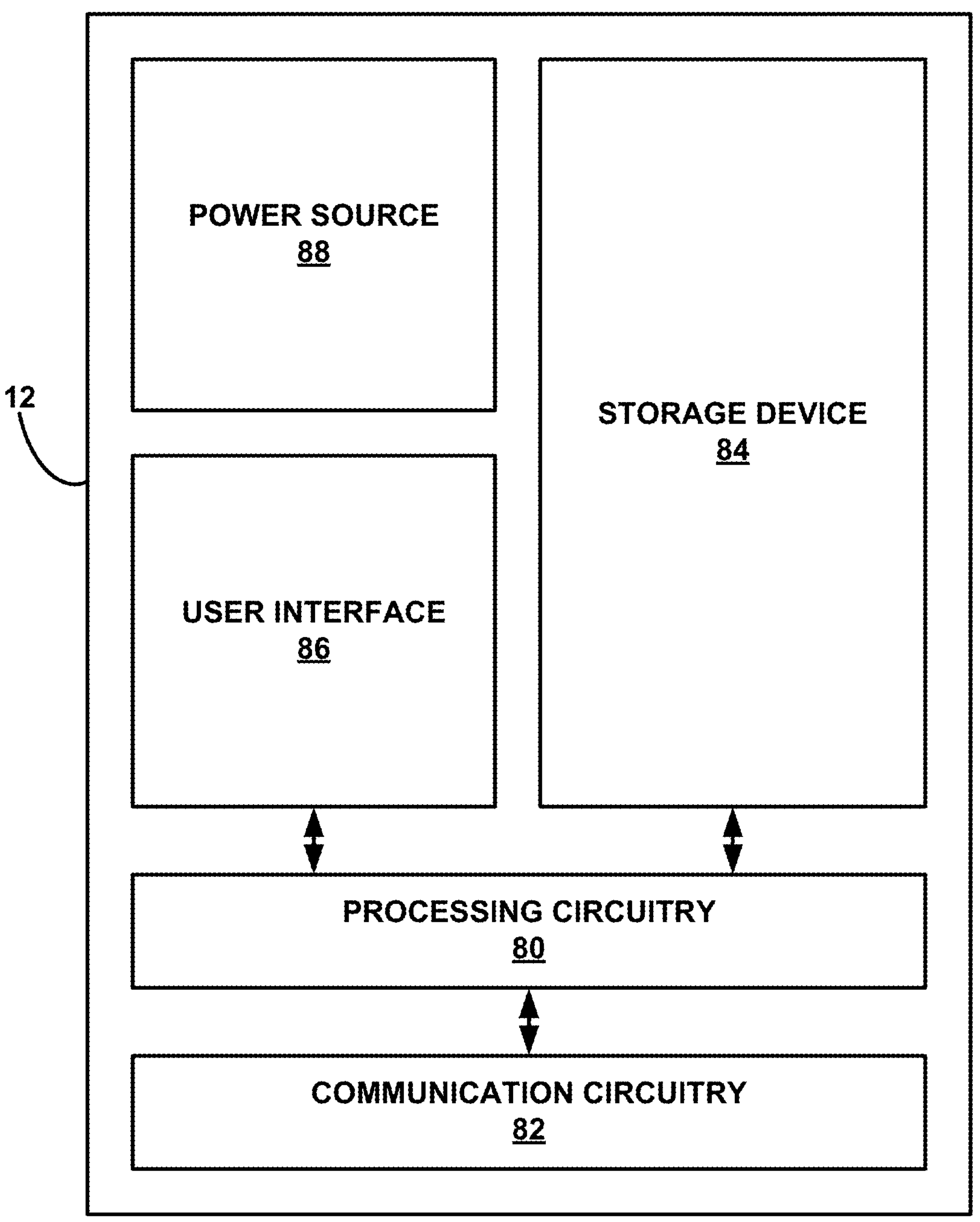
FIG. 5 is a functional block diagram illustrating an example configuration of components of the external device of FIG. 1, in accordance with one or more techniques of this disclosure.

FIG. 5 is a block diagram illustrating an example configuration of components of external device 12, in accordance with one or more techniques of this disclosure. In the example of FIG. 5, external device 12 includes processing circuitry 80, communication circuitry 82, storage device 84, user interface 86, and power source 88.

Processing circuitry 80, in one example, may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as IMD 10. Under the control of processing circuitry 80, communication circuitry 82 may receive downlink telemetry from, as well as send uplink telemetry to, IMD 10, or another device.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, DRAM, SRAM, magnetic discs, optical discs, flash memories, or forms of EPROM or EEPROM. In some examples, storage device 84 is used to store data indicative of instructions for execution by processing circuitry 80. Storage device 84 may be used by software or applications running on external device 12 to temporarily store information during program execution.

Data exchanged between external device 12 and IMD 10 may include operational parameters. External device 12 may transmit data including computer readable instructions which, when implemented by IMD 10, may control IMD 10 to change one or more operational parameters and/or export collected data. For example, processing circuitry 80 may transmit an instruction to IMD 10 which requests IMD 10 to export collected data (e.g., data corresponding to impedance measurements) to external device 12. In turn, external device 12 may receive the collected data from IMD 10 and store the collected data in storage device 84. Additionally, or alternatively, processing circuitry 80 may export instructions to IMD 10 requesting IMD 10 to update electrode combinations for stimulation or sensing.

A user, such as a clinician or patient 4, may interact with external device 12 through user interface 86. User interface 86 includes a display (not shown), such as an LCD or LED display or other type of screen, with which processing circuitry 80 may present information related to IMD 10 (e.g., EGM signals obtained from at least one electrode or at least one electrode combination). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to patient 4, receiving voice commands from patient 4, or both. Storage device 84 may include instructions for operating user interface 86 and for managing power source 88.

Power source 88 is configured to deliver operating power to the components of external device 12. Power source 88 may include a battery and a power generation circuit to produce the operating power. In some examples, the battery is rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within external device 12. In other examples, traditional batteries (e.g., nickel cadmium or lithium ion batteries) may be used. In addition, external device 12 may be directly coupled to an alternating current outlet to operate.

Figure 6:
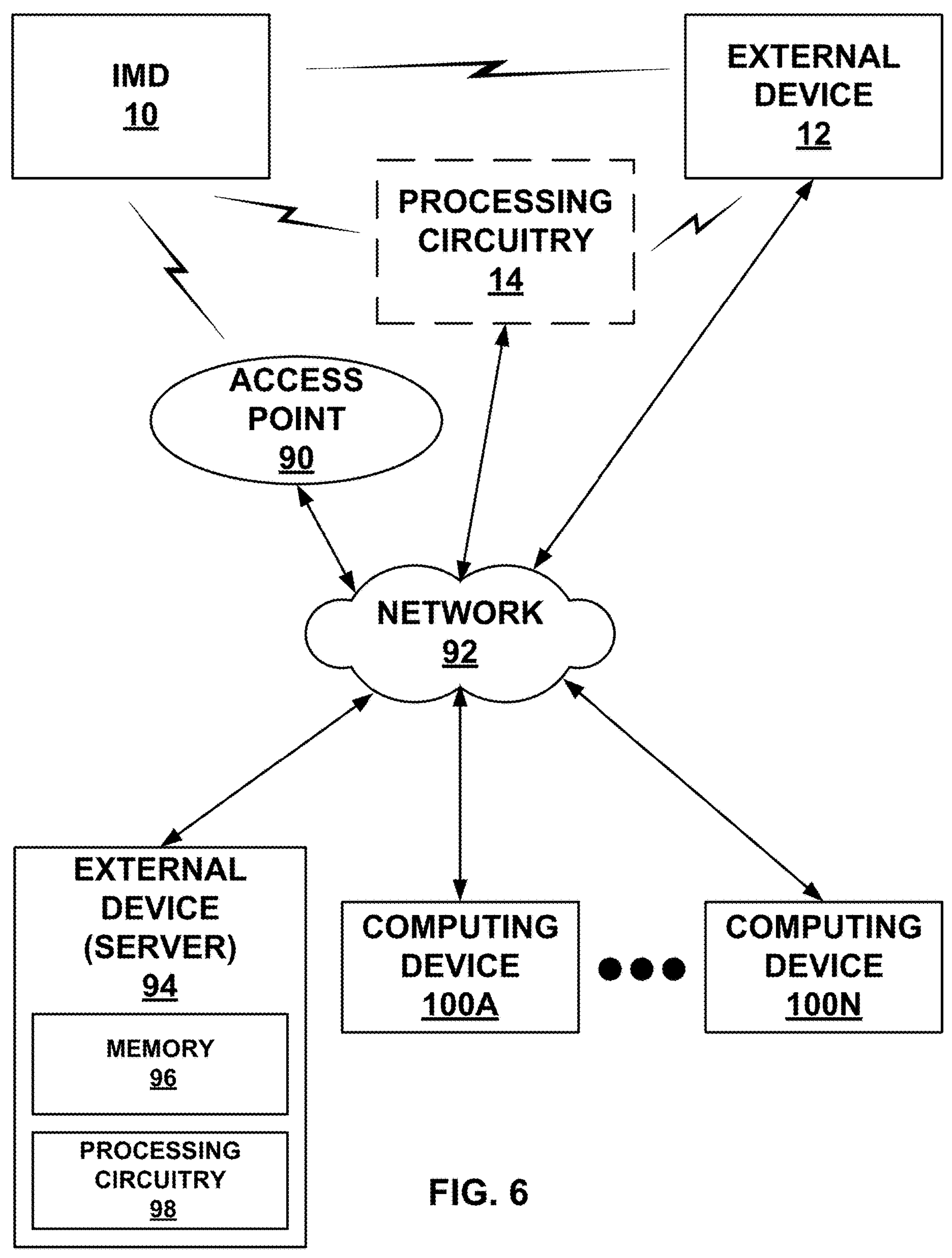
FIG. 6 is a block diagram illustrating an example system that includes an access point, a network, external computing devices, such as a server, and one or more other computing devices, which may be coupled to the IMD of FIGS. 1-4, an external device, and processing circuitry via a network, in accordance with one or more techniques described herein.

FIG. 6 is a block diagram illustrating an example system that includes an access point 90, a network 92, external computing devices, such as a server 94, and one or more other computing devices 100A-100N, which may be coupled to IMD 10, external device 12, and processing circuitry 14 via network 92, in accordance with one or more techniques described herein. In this example, IMD 10 may use communication circuitry 54 to communicate with external device 12 via a first wireless connection, and to communication with an access point 90 via a second wireless connection. In the example of FIG. 6, access point 90, external device 12, server 94, and computing devices 100A-100N are interconnected and may communicate with each other through network 92.

Access point 90 may include a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. As discussed above, IMD 10 may be configured to transmit data, such as current values and heart failure statuses, to external device 12. In addition, access point 90 may interrogate IMD 10, such as periodically or in response to a command from the patient or network 92, in order to retrieve parameter values determined by processing circuitry 50 of IMD 10, or other operational or patient data from IMD 10. Access point 90 may then communicate the retrieved data to server 94 via network 92.

In some cases, server 94 may be configured to provide a secure storage site for data that has been collected from IMD 10, and/or external device 12. In some cases, server 94 may assemble data in web pages or other documents for viewing by trained professionals, such as clinicians, via computing devices 100A-100N. One or more aspects of the illustrated system of FIG. 6 may be implemented with general network technology and functionality, which may be similar to that provided by the Medtronic CareLink® Network developed by Medtronic plc, of Dublin, Ireland.

In some examples, one or more of computing devices 100A-100N (e.g., device 100A) may be a tablet or other smart device located with a clinician, by which the clinician may program, receive alerts from, and/or interrogate IMD 10. For example, the clinician may access data corresponding to parameter measurements performed by IMD 10 through device 100A, such as when patient 4 is in between clinician visits, to check on a status of a medical condition. In some examples, the clinician may enter instructions for a medical intervention for patient 4 into an app in device 100A, such as based on a status of a patient condition determined by IMD 10, external device 12, processing circuitry 14, or any combination thereof, or based on other patient data known to the clinician. Device 100A then may transmit the instructions for medical intervention to another of computing devices 100A-100N (e.g., device 100B) located with patient 4 or a caregiver of patient 4. For example, such instructions for medical intervention may include an instruction to change a drug dosage, timing, or selection, to schedule a visit with the clinician, or to seek medical attention. In further examples, device 100B may generate an alert to patient 4 based on a status of a medical condition of patient 4 determined by IMD 10, which may enable patient 4 proactively to seek medical attention prior to receiving instructions for a medical intervention. In this manner, patient 4 may be empowered to take action, as needed, to address his or her medical status, which may help improve clinical outcomes for patient 4.

Figure 7:
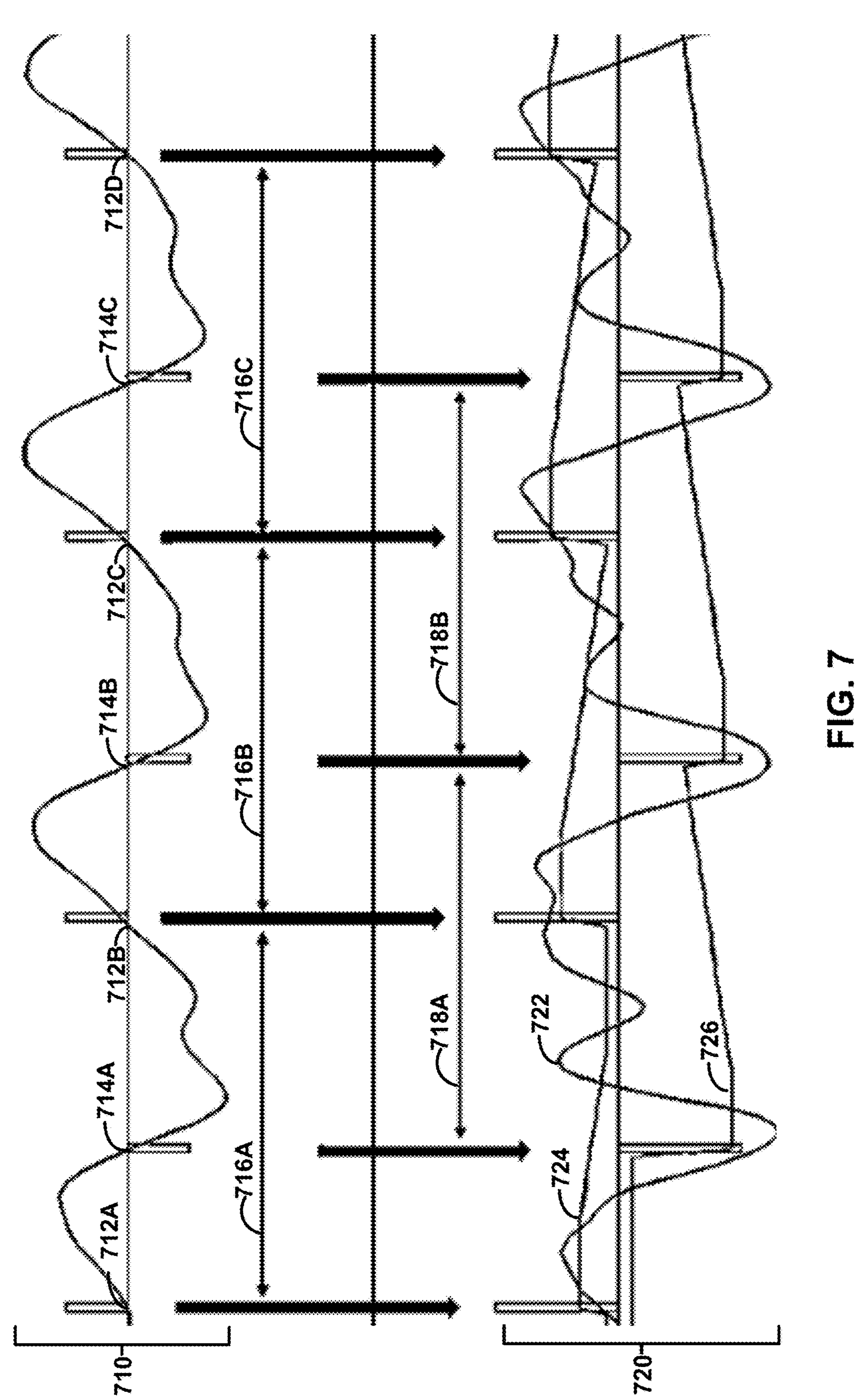
FIG. 7 is a graph illustrating an impedance plot and an impedance derivative plot, in accordance with one or more techniques described herein.

FIG. 7 is a graph illustrating an impedance plot 710 and an impedance derivative plot 720 in accordance with one or more techniques of this disclosure. Impedance plot 710 includes positive zero crossings 712A-712D (collectively, "positive zero crossings 712") and negative zero crossings 714A-714D (collectively, "negative zero crossings 714"). Additionally, FIG. 7 illustrates respiration intervals derived from positive zero crossings 716A-716C (collectively, "respiration intervals 716") and respiration intervals derived from negative zero crossings 718A-718B (collectively, "respiration intervals 718"). Impedance derivative plot 720 includes derivative signal 722, positive auto-adjusting threshold 724, and negative auto-adjusting threshold 726. For convenience, FIG. 7 is described with respect to IMD 10, external device 12, and processing circuitry 14 of FIGS. 1-5. However, the techniques of FIG. 7 may be performed by different components of IMD 10 or by additional or alternative medical devices.

Impedance plot 710 may represent a graph of a set of impedance values, and impedance derivative plot 720 may represent a derivative of the first set of impedance values. In this way, impedance derivative plot 720 may reflect a slope of impedance plot 710 for each impedance value of the set of impedance values. Processing circuitry 14 may be configured to identify positive zero crossings 712 and negative zero crossings 714. Processing circuitry 14 may be configured to determine respiration intervals 716, where each of respiration intervals 716 represent an amount of time between a respective pair of consecutive positive zero crossings. For example, respiration interval 716A represents an amount of time between positive zero crossing 712A and positive zero crossing 712B, respiration interval 716B represents an amount of time between positive zero crossing 712B and positive zero crossing 712C, and respiration interval 716C represents an amount of time between positive zero crossing 712C and positive zero crossing 712D. Additionally, processing circuitry 14 may be configured to determine respiration intervals 718, where each of respiration intervals 718 represent an amount of time between a respective pair of consecutive negative zero crossings. For example, respiration interval 718A represents an amount of time between negative zero crossing 714A and negative zero crossing 714B and respiration interval 718B represents an amount of time between negative zero crossing 714B and negative zero crossing 714C.

In order to determine that a detected positive zero crossing 712 or negative zero crossing 714 in impedance plot 710 is valid, processing circuitry 14 may compare a corresponding point in impedance derivative plot 720 with positive auto-adjusting threshold 724 and negative auto-adjusting threshold 726, respectively. For example, processing circuitry 14 may determine that positive zero crossing 712B is valid, because derivative signal 722 is greater than positive auto-adjusting threshold 724 at a time in which positive zero crossing 712B occurs. Additionally, for example, processing circuitry 14 may determine that negative zero crossing 714B is valid because derivative signal 722 is less than negative auto-adjusting threshold 726 at a time in which negative zero crossing 714B occurs. By comparing derivative signal 722 with auto-adjusting thresholds 724, 726, processing circuitry 14 may improve an accuracy in which respiration intervals are identified.

In some examples, impedance plot 710 represents the second set of secondary impedance values as described above with respect to FIG. 1. Additionally, in some examples, impedance derivative plot 720 represents the third set of secondary impedance values as described above with respect to FIG. 1. Processing circuitry 14 may determine positive zero crossings 712 and negative zero crossings 714 based on the second set of secondary impedance values (e.g., impedance plot 710) and the third set of secondary impedance values (e.g., impedance derivative plot 720) according to one or more techniques described above with respect to FIG. 1.

Figure 8:
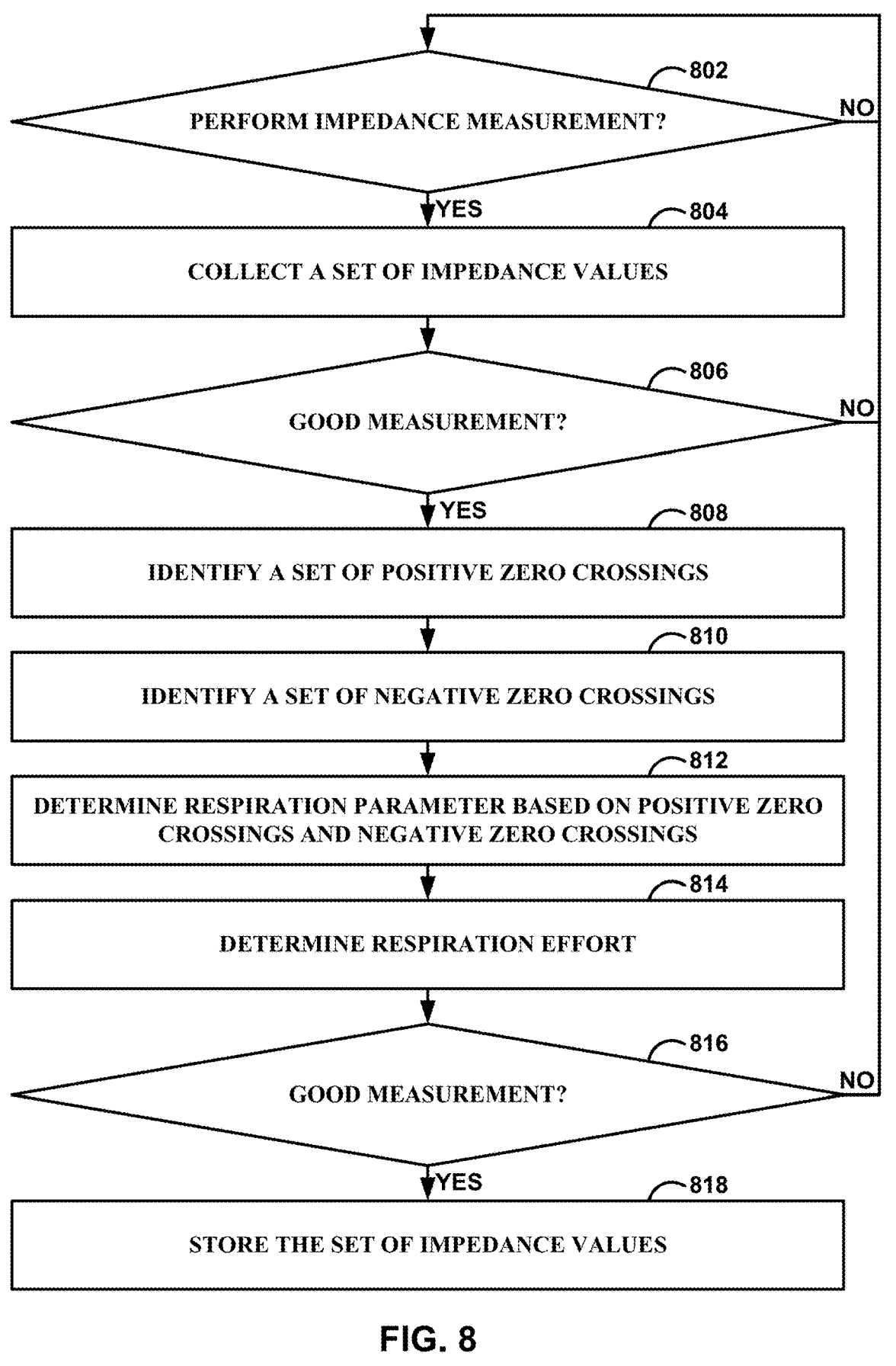

FIG. 8 is a flow diagram illustrating an example operation for performing parameter measurements, in accordance with one or more techniques of this disclosure. For convenience, FIG. 8 is described with respect to IMD 10, external device 12, and processing circuitry 14 of FIGS. 1-5. However, the techniques of FIG. 8 may be performed by different components of IMD 10 or by additional or alternative medical devices.

IMD 10 may, in some examples, be an ICM implanted in patient 4 that measures patient parameters for analysis to identify or monitor one or more patient conditions such as heart failure, sleep apnea, or COPD. For example, IMD 10 may perform a set of impedance measurements, where each impedance measurement produces impedance data consisting of a set of impedance values. In some cases, the impedance data may be indicative of one or more physiological functions of patient 4, such as any combination of cardiac functions, respiratory functions, and intestinal functions. For example, processing circuitry 14 may process the impedance data to determine one or more parameters (e.g., respiratory rate, respiratory rate variability, and respiratory effort) associated with respiratory cycles of the patient. In turn, processing circuitry 14 may analyze such parameters to identify or monitor one or more medical conditions. Since it may be beneficial to track respiratory parameters over an extended period of time, IMD 10 may, in some examples, perform impedance measurements at an impedance measurement rate, as described in further detail below.

In some examples, IMD 10 performs impedance measurements according to an impedance measurement schedule that is uploaded to IMD 10 by external device 12 or another device. The impedance measurement schedule may, in some cases, be stored in storage device 56 of IMD 10. In some examples, the impedance measurement schedule may include an instruction to perform impedance measurements at an impedance measurement rate (e.g., one measurement per hour, one measurement per day, one measurement per month, or any other valid rate). Additionally, in some examples, the impedance measurement schedule includes instructions to perform impedance measurements based on a time of day. For example, the impedance measurement may include instructions to perform impedance measurements only at daytime (e.g., from 8 AM to 8 PM), only at nighttime (e.g., from 12 AM to 6 AM), or instructions to perform impedance measurements at a first measurement rate during the daytime and perform impedance measurements at a second measurement rate during the nighttime, where the first measurement rate is different from the second measurement rate. Each impedance measurement may last for a measurement duration, where the measurement duration may be set based on instructions received by IMD 10 from external device 12 or another device. In some examples, the measurement duration is within a range between 10 seconds and 60 seconds (e.g., 32 seconds). In this way, each impedance measurement may capture a plurality of respiratory cycles, where each respiratory cycle includes an inhale phase and an exhale phase.

Additionally, since it may be beneficial to perform impedance measurements under certain conditions, IMD 10 may, in some examples, perform impedance measurements in response to a set of patient parameters, as described in further detail below. In some examples, the set of patient parameters includes any combination of a heart rate of patient 4, a posture of patient 4, an activity level of patient 4, an electrocardiogram (ECG) corresponding to patient 4, a presence or an absence of one or more arrhythmias, patient triggers, and data from an acoustic sensor. IMD 10 may measure each parameter of the set of patient parameters at a respective parameter measurement rate. The parameter measurement rate corresponding to each patient parameter of the set of patient parameters may, in some cases, be stored in storage device 56 of IMD 10.

At block 802, IMD 10 may determine whether to perform an impedance measurement. In some examples, IMD 10 determines whether to perform the measurement based on the impedance measurement schedule which is stored in storage device 56. Additionally, in some examples, IMD 10 determines whether to perform the impedance measurement based on a set of patient parameters. If IMD 10 determines not to perform an impedance measurement ("NO" branch of block 802), IMD 10 continues to determine whether to perform an impedance measurement. If IMD 10 determines to perform an evaluation ("YES" branch of block 802), IMD 10 proceeds to collect a set of impedance values (804). In some examples, IMD 10 collects the set of impedance values at a sampling rate between 100 Hz and 300 Hz. In some cases, the sampling rate is 128 Hz. In other cases, the sampling rate is 256 Hz. In some examples, each impedance value of the set of impedance values defines a resolution between 10 bits and 20 bits (e.g., 14 bits). IMD 10 may, in some cases truncate each impedance value from a first resolution to a second resolution (e.g., from 14 bits to 12 bits).

After IMD 10 collects the set of impedance values, processing circuitry 14 may determine, based on the set of impedance values, whether the impedance measurement is a good impedance measurement (806). Processing circuitry 14 may determine whether the impedance measurement is a good measurement by comparing a maximum impedance value of the set of impedance values, a minimum impedance value of the set of impedance values, a difference between the maximum impedance value and the minimum impedance value, or a mean impedance value of the set of impedance values with a respective impedance threshold. For example, if a difference between the maximum impedance value and the minimum impedance value is greater than a respective threshold (e.g., a "noise" threshold), then processing circuitry 14 may determine that a quality of the impedance measurement is sufficient to continue processing the set of impedance values. If processing circuitry 14 determines that the impedance measurement is not a good measurement ("NO" branch of block 806), the example operation may return to block 802. If processing circuitry 14 determines that the impedance measurement is a good measurement ("YES" branch of block 806), the example operation may proceed to block 808.

Processing circuitry 14 may be configured to identify a set of positive zero crossings (808) and identify a set of negative zero crossings (810) in the set of impedance values. In some examples, processing circuitry 14 may process the set of impedance values to filter out high-frequency and low-frequency components, and center the set of impedance values around a y=002 axis. For example, the processed impedance values may represent an impedance signal that oscillates about the y=052 axis as patient 4 inhales and exhales. As such, the processed impedance values may periodically transition from a negative value to a positive value (e.g., a negative-going-positive occurrence) or transition from a positive value to a negative value (e.g., a positive-going-negative occurrence). To determine the set of positive zero crossings and the set of negative zero crossings, in some cases, processing circuitry 14 may determine whether each negative-going-positive occurrence satisfies a first set of conditions and if each positive-going-negative occurrence satisfies a second set of conditions. Processing circuitry 14 may determine that negative-going-positive occurrences that satisfy the first set of conditions represent the set of positive zero crossings and that positive-going-negative occurrences that satisfy the second set of conditions represent the set of negative zero crossings.

Processing circuitry 14 determines one or more respiration parameters based on the set of positive zero crossings and the set of negative zero crossings (812). For example, processing circuitry 14 may determine a respiration rate and a respiration rate variability using the set of positive zero crossings and the set of negative zero crossings. Since the processed set of impedance values may represent an oscillating signal indicative of respiratory patterns of patient 4, a single respiration cycle may be given by an amount of time separating consecutive positive zero crossings of the set of positive zero crossings or an amount of time separating consecutive negative zero crossings of the set of negative zero crossings. As such, processing circuitry 14 may determine a set of respiration cycles, or respiration intervals based on the set of positive zero crossings and the set of negative zero crossings. Using the set of respiration cycles, processing circuitry 14 may calculate a mean respiration cycle, determine a median respiration cycle, calculate a variability in the set of respiration, or any combination thereof. To calculate a respiration rate corresponding to the set of impedance values collected during a respective impedance measurement, for example, processing circuitry 14 may calculate a respiration rate corresponding to a median respiration cycle of the set of respiration cycles.

Processing circuitry 14 determines a respiration effort (814) based on, in some examples, the set of positive zero crossings, the set of negative zero crossings, and the set of impedance values. Respiration effort may, at least in part, be given by an amplitude of the impedance signal represented by the set of impedance values. In other words deeper breathing may result in greater impedance signal amplitudes than shallower breathing. In some cases, processing circuitry 14 may determine a single respiration effort value corresponding to the set of impedance values.

At block 816, processing circuitry 14 may determine whether the impedance measurement producing the set of impedance values is a good measurement. To determine whether the impedance measurement is a good measurement, processing circuitry 14 may compare a set of parameter values (e.g., a motion level associated with patient 4, respiration effort, heart rate, heart rate variability, ambient light, or any combination thereof) associated with the impedance measurement with respective threshold parameter values. Additionally, or alternatively, in some cases, processing circuitry 14 may determine whether the parameter measurement satisfies a set of conditions. If processing circuitry 14 determines that the impedance measurement is not a good measurement ("NO" branch of block 816), the operation returns to block 802 and IMD 10 determines whether to perform another impedance measurement. If processing circuitry 14 determines that the impedance measurement is a good measurement ("YES" branch of block 816), processing circuitry 14 stores the set of impedance values (818). In some examples, processing circuitry 14 stores the set of impedance values in storage device 56 of IMD 10, storage device 84 of external device 12, or another storage device not pictured in FIGS. 1-5. Additionally, in some examples, processing circuitry 14 may store the set of respiration intervals (e.g., a group of respiration intervals derived from positive zero crossings (Pi) and a group of respiration intervals derived from negative zero crossings (Ni).

Figure 9:
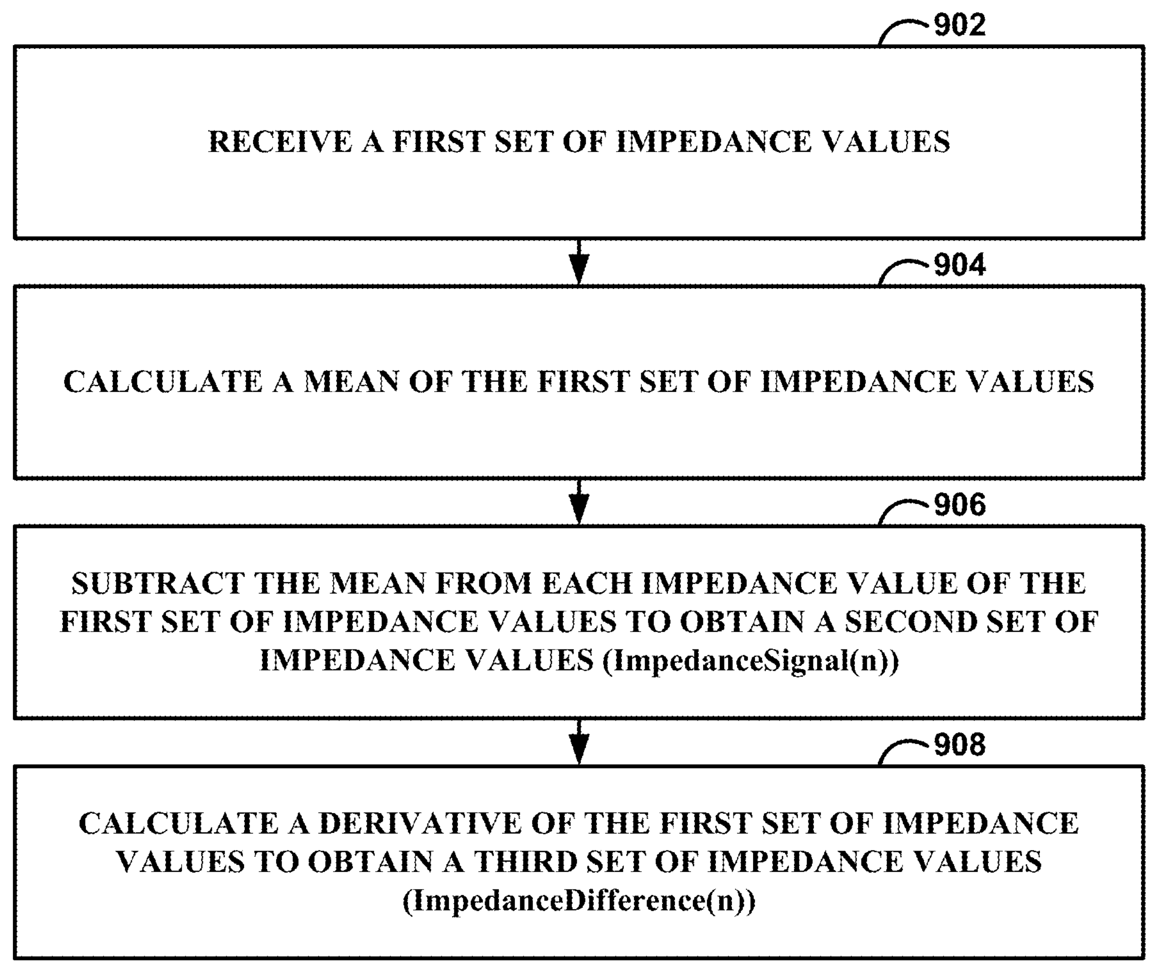
FIG. 9 is a flow diagram illustrating an example operation for processing a set of impedance values, in accordance with one or more techniques of this disclosure.
Figure 10:
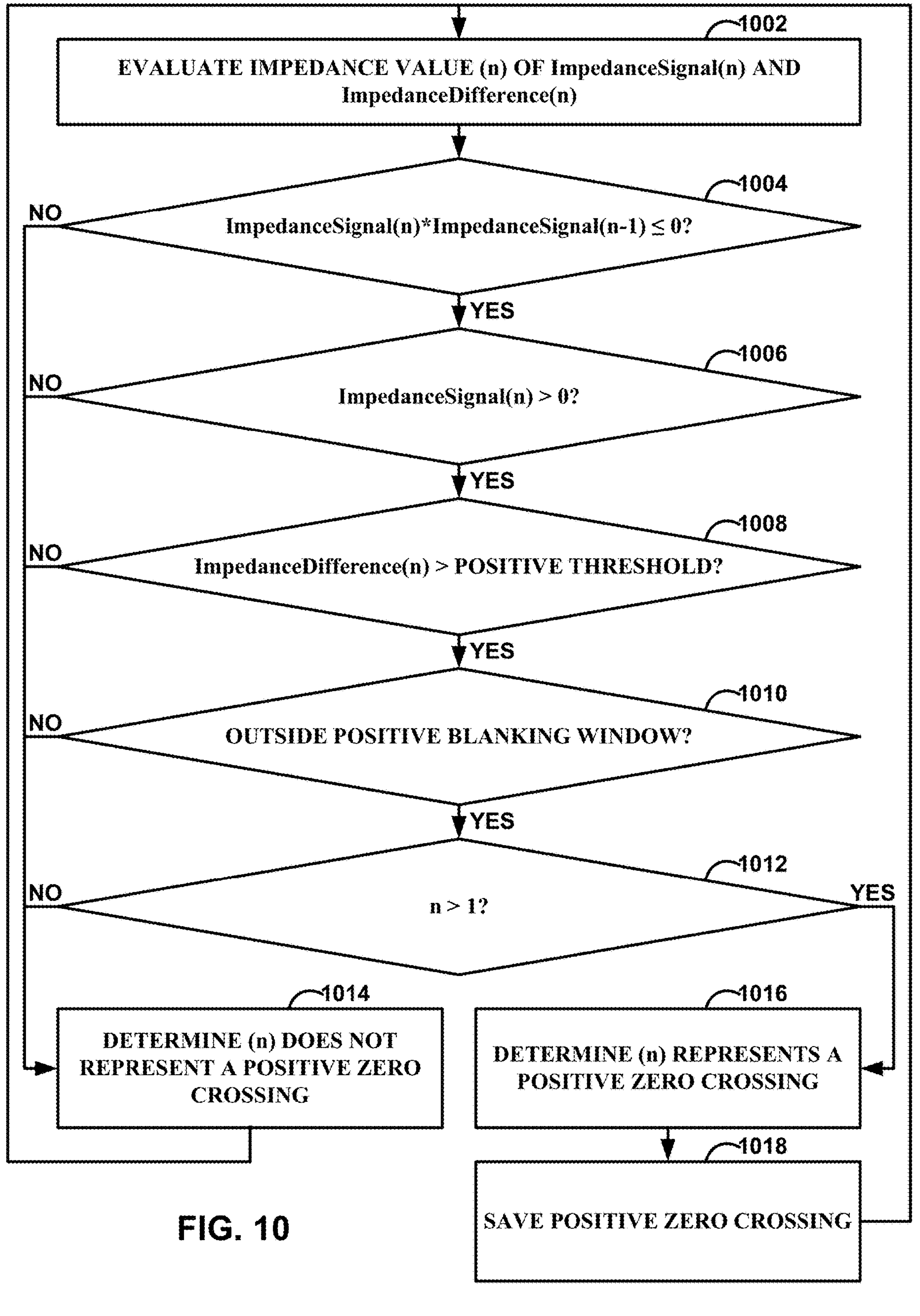
FIG. 10 is a flow diagram illustrating an example operation for determining a set of positive zero crossings in an impedance measurement, in accordance with one or more techniques of this disclosure.
Figure 11:
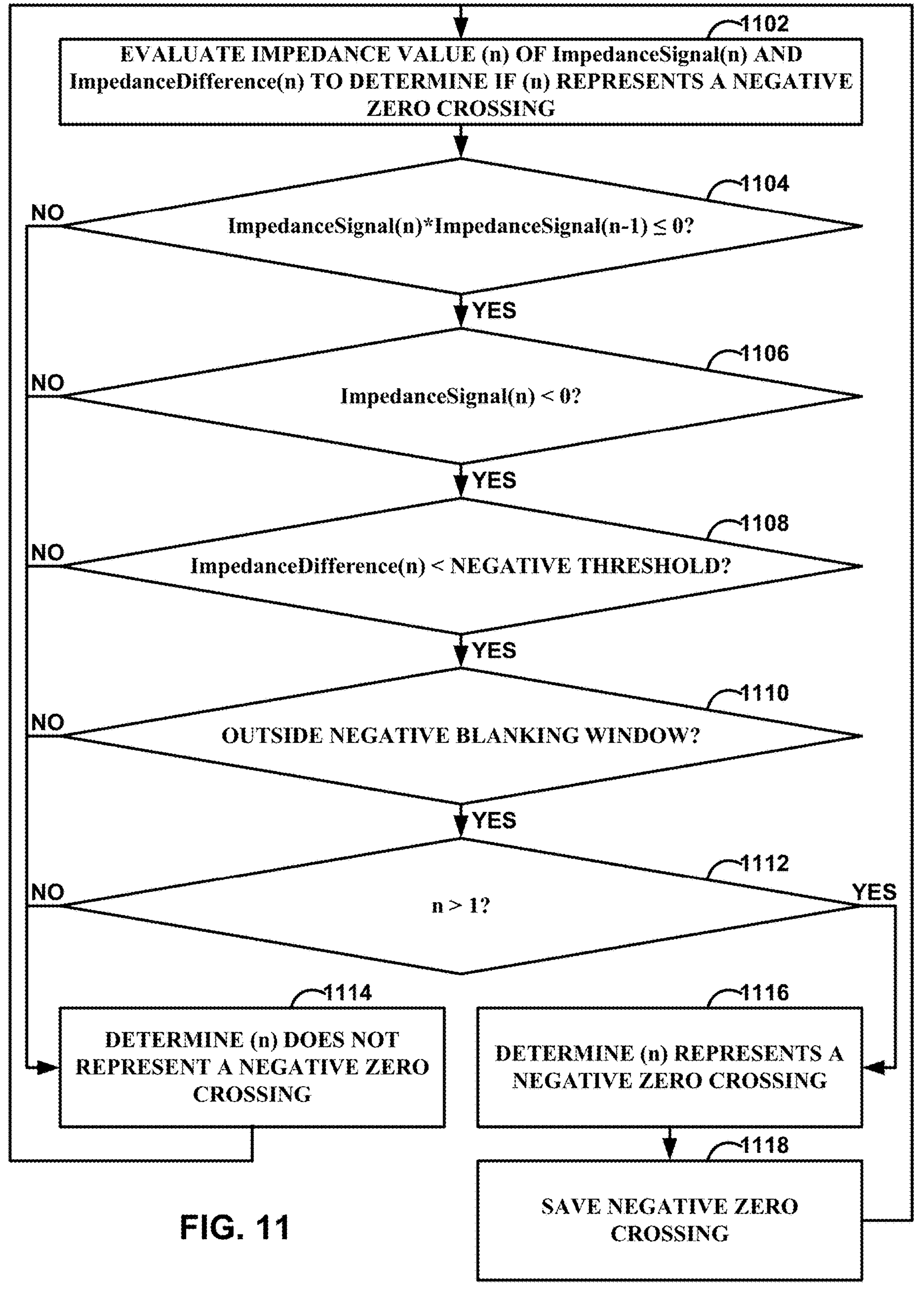
FIG. 11 is a flow diagram illustrating an example operation for determining a set of negative zero crossings in an impedance measurement, in accordance with one or more techniques of this disclosure.

FIGS. 9-11 illustrate example operations for identifying a set of positive zero crossings and a set of negative zero crossings based on a set of impedance values, by first processing the set of impedance values.

FIG. 9 is a flow diagram illustrating an example operation for processing a set of impedance values, in accordance with one or more techniques of this disclosure. For convenience, FIG. 9 is described with respect to IMD 10, external device 12, and processing circuitry 14 of FIGS. 1-5. However, the techniques of FIG. 9 may be performed by different components of IMD 10, external device 12, processing circuitry 14, or by additional or alternative medical devices.

When IMD 10 performs an impedance measurement, IMD may collect a set of impedance values which represent an impedance signal over a period of time. The set of impedance values collected by IMD 10 may be referred to as the "raw impedance signal." The impedance signal may be analyzed by processing circuitry 14 in order to determine respiratory parameters, such as respiratory rate, respiratory rate variability, and respiratory effort, as examples. In some examples, it may be beneficial for processing circuitry 14 to process the raw impedance signal before analyzing the impedance values to determine respiratory parameters.

As illustrated in FIG. 9, processing circuitry 14 receives a first set of impedance values (902). Processing circuitry 14 may, in some cases, represent processing circuitry 50 of IMD 10. In such cases, processing circuitry 50 may access storage device 56 to obtain the first set of impedance values. Additionally, in some cases, processing circuitry 14 represents processing circuitry 80 of external device 12. In such cases, processing circuitry 50 may access storage device 56, access storage device 84, or access another storage device to obtain the first set of impedance values. The first set of impedance values may represent impedance data corresponding to an impedance measurement. Additionally, in some cases, the first set of impedance values may include a timestamp which indicates a time in which the respective impedance measurement was taken. In some examples, each pair of consecutive impedance values of the first set of impedance values is separated by a sampling interval. In other words, the first set of impedance values may define a sampling rate. The sampling rate may be within a range between 5 Hz and 15 Hz (e.g., 8 Hz) and a duration of the first set of impedance values may be within a range between 10 seconds and 60 seconds (e.g., 32 seconds).

Processing circuitry 14 calculates a mean impedance value corresponding to each impedance value of the first set of impedance values (904) and subtracts the respective mean impedance value from each impedance value of the first set of impedance values to obtain a second set of impedance values (906). In some examples, the mean impedance value corresponding to each impedance value of the first set of impedance values represents a mean impedance value of the first set of impedance values. In such examples, the second set of impedance values may resemble the first set of impedance values when the sets are plotted, with the second set of impedance values being offset by the mean impedance value on the y-axis. Such an offset may center the second set of impedance values about a y=0Ω axis. Consequently, since the impedance data may, in some cases, show an oscillation representative of patient 4 inhaling and exhaling, the second set of impedance values may oscillate about the y=0Ω axis. In some examples, the mean impedance value corresponding to each impedance value of the first set of impedance values represents a moving average of the first set of impedance values. For example, processing circuitry 14 may apply an m-sample moving average, where the respective mean impedance value corresponding to each impedance value represents a mean impedance value of m (e.g., m=64 when first set of impedance values is sampled at 8 Hz) impedance values preceding the respective impedance value. Additionally, in some cases, processing circuitry 14 may apply a high pass filter to the first set of impedance values in order to obtain the second set of impedance values. In the example operation of FIG. 9, the second set of impedance values is represented by ImpedanceSignal(n), where the second set of impedance values is n impedance values in length.

After obtaining the second set of impedance values, processing circuitry 14 calculates a derivative of the first set of impedance values to obtain a third set of impedance values (908). For example, to calculate the derivative, processing circuitry 14 may determine a difference value associated with each impedance value of the first set of impedance values. Each difference value may represent a difference between a first impedance value preceding the respective impedance value and a second impedance value following the respective impedance value. In some examples, processing circuitry 14 sets the first three impedance values of the third set of impedance values to zero. In the example operation of FIG. 9, the third set of impedance values is represented by ImpedanceDifference(n), where the third set of impedance values is n impedance values in length.

FIG. 10 is a flow diagram illustrating an example operation for determining a set of positive zero crossings in an impedance measurement, in accordance with one or more techniques of this disclosure. For convenience, FIG. 10 is described with respect to IMD 10, external device 12, and processing circuitry 14 of FIGS. 1-5. However, the techniques of FIG. 10 may be performed by different components of IMD 10, external device 12, processing circuitry 14, or by additional or alternative medical devices.

In some examples, processing circuitry 14 determines one or more respiration parameters based, at least in part, on a set of positive zero crossings. For example, processing circuitry 14 may determine a set of respiration intervals based on the set of positive zero crossings. Processing circuitry 14 may determine the set of positive zero crossings in impedance data collected by IMD 10, where the impedance data is collected during an impedance measurement. IMD 10 may, in some examples, be an ICM implanted in patient 4 that measures patient parameters for analysis to identify or monitor one or more patient conditions such as heart failure, sleep apnea, or COPD. For example, IMD 10 may perform a set of impedance measurements, where each impedance measurement produces impedance data consisting of a set of impedance values. In some cases, the impedance data may be indicative of one or more physiological functions of patient 4, such as any combination of cardiac functions, respiratory functions, and intestinal functions. For example, processing circuitry 14 may process the impedance data to determine one or more parameters (e.g., respiratory rate, respiratory rate variability, and respiratory effort) associated with respiratory cycles of the patient, as discussed in further detail below. In turn, processing circuitry 14 may analyze such parameters to identify or monitor one or more medical conditions. To determine the set of positive zero crossings, processing circuitry 14 may determine whether each negative-going-positive occurrence in the second set of impedance values (ImpedanceSignal(n)) satisfies a set of conditions. In the example operation of FIG. 10, the set of conditions may include the decisions of blocks 1004-1012, as described in further detail below.

As illustrated in FIG. 10, processing circuitry 14 may evaluate an impedance value n of the second set of impedance values (e.g., impedanceSignal(n)) and a corresponding impedance value of the third set of impedance values (e.g., impedanceDifference(n)) (1002) to determine if n represents a positive zero crossing (e.g., a positive zero crossing 712 as illustrated in FIG. 7). In some examples, the second set of impedance values and the first set of impedance values may be calculated based on a first set of impedance values collected by IMD 10 (e.g., raw impedance data).

At block 1004, processing circuitry 14 may determine, for each impedance value of the second set of impedance values, whether a multiplication of two consecutive impedance values of the second set of impedance values (e.g., impedanceSignal(n)·impedanceSignal(n−1)) is less than or equal to zero. In some examples, if the multiplication of two consecutive impedance values of the second set of impedance values is less than or equal to zero, this may indicate that one of impedanceSignal(n) and impedanceSignal(n−1) is negative and one of impedanceSignal(n) and impedanceSignal(n−1) is positive. Additionally, in some examples, if the multiplication of two consecutive impedance values of the second set of impedance values is less than or equal to zero, this may indicate that at least one of impedanceSignal(n) and impedanceSignal(n−1) is equal to zero. As such, by multiplying two consecutive impedance values, processing circuitry 14 may determine whether the respective consecutive impedance values represent a zero crossing event. If the multiplication of two consecutive impedance values of the second set of impedance values is not less than or equal to zero ("NO" branch of block 1004), processing circuitry 14 determines that the respective consecutive impedance values do not satisfy the condition of block 1004, and processing circuitry 14 determines that impedanceSignal(n) does not represent a positive zero crossing (1014). If the multiplication of two consecutive impedance values of the second set of impedance values is less than or equal to zero ("YES" branch of block 1004), processing circuitry 14 determines that the respective consecutive impedance values satisfy the condition of block 1004, and processing circuitry 14 proceeds to evaluate the condition of block 1006. Additionally, or alternatively, in some cases, processing circuitry may monitor impedanceSignal for sign changes at block 1004. If a sign change is detected, the condition of block 1004 is satisfied and if a sign change is not detected, the condition of block 1004 is not satisfied.

At block 1006, processing circuitry 14 may determine whether a lead impedance value (e.g., impedanceSignal(n)) of a pair of consecutive impedance values is greater than zero, where the pair of consecutive impedance values (e.g., impedanceSignal(n) and impedanceSignal(n−1)) represent a zero crossing event identified by processing circuitry 14 at block 1004. If processing circuitry 14 determines that the lead impedance value is not greater than zero ("NO" branch of block 1006), processing circuitry 14 determines that the respective consecutive impedance values do not satisfy the condition of block 1006, and processing circuitry 14 determines that impedanceSignal(n) does not represent a positive zero crossing (1014). If processing circuitry 14 determines that the lead impedance value is greater than zero ("YES" branch of block 1006), processing circuitry 14 determines that the load impedance value satisfies the condition of block 1006 and processing circuitry 14 proceeds to evaluate the condition of block 1008.

At block 1008, processing circuitry 14 may determine, if a difference impedance value of the third set of impedance values (e.g., ImpedanceDifference(n)) is greater than a positive threshold difference value (e.g., POSITIVE THRESHOLD). The difference impedance value may, in some cases, represent a slope associated with a lead impedance value (e.g., impedanceSignal(n)) of a pair of consecutive impedance values that processing circuitry 14 determines to be a zero crossing event in block 1004. If processing circuitry 14 determines that the difference impedance value is not greater than the positive threshold difference value ("NO" branch of block 1008), processing circuitry 14 determines that the respective consecutive impedance values do not satisfy the condition of block 1008, and processing circuitry 14 determines that impedanceSignal(n) does not represent a positive zero crossing (1014). If processing circuitry 14 determines that the difference impedance value is greater than the positive threshold difference value ("YES" branch of block 1008), processing circuitry 14 determines that the lead impedance value satisfies the condition of block 1008 and processing circuitry 14 proceeds to evaluate the condition of block 1010. In some examples, POSITIVE THRESHOLD may be represented by positive auto-adjusting threshold 724 of FIG. 7.

At block 1010, processing circuitry 14 may determine whether the lead impedance value (e.g., impedanceSignal (n)) of the respective pair of consecutive impedance values that satisfies the conditions of blocks 1004-1008 is outside of a positive blanking window. To determine whether the lead impedance value is outside of the positive blanking window, processing circuitry 14 determines whether the lead impedance value is outside of a group of consecutive secondary impedance values immediately preceding the secondary impedance value n, where the group of consecutive secondary impedance values represents the positive blanking window. In some examples, the group of consecutive secondary impedance values includes a number of consecutive secondary impedance values within a range between 5 and 15 (e.g., 10). If a positive zero crossing exists within the group of consecutive secondary impedance values, processing circuitry 14 may determine that impedanceSignal(n) is not outside of the positive blanking window ("NO" branch of block 1010), determine that the condition of block 1010 is not satisfied for the secondary impedance value n, and determine that that impedanceSignal(n) does not represent a positive zero crossing (1014). If a positive zero crossing does not exist within the group of consecutive secondary impedance values, processing circuitry 14 may determine that impedanceSignal(n) is outside of the positive blanking window ("YES" branch of block 1010), determine that the condition of block 1010 is satisfied for the secondary impedance value n, and proceed to evaluate the condition of block 1012. In this way, a positive blanking window may follow each valid positive zero crossing. If a potential positive zero crossing occurs within a blanking window following a valid positive zero crossing, processing circuitry 14 may determine that the potential positive zero crossing is invalid (e.g., does not represent a valid positive zero crossing).

At block 1012, processing circuitry 14 may determine whether n is greater than one. If n is not greater than 1, processing circuitry 14 may determine that the condition of block 1012 is not satisfied and determine that impedanceSignal(n) does not represent a positive zero crossing (1014). If n is greater than 1, processing circuitry 14 may determine that the condition of blocks 1004-1012 are satisfied and determine that impedanceSignal(n) represents a positive zero crossing (1016). Subsequently, processing circuitry 14 may save the positive zero crossing (1018) in a storage device (e.g., storage device 56, storage device 84, or another storage device) as a part of the set of positive zero crossings.

Processing circuitry 14 may, in some examples, evaluate every pair of consecutive impedance values of the second set of impedance values to determine whether each respective pair of consecutive impedance values represents a positive zero crossing (e.g., a positive zero crossing 712 as illustrated in FIG. 7). The conditions of blocks 1004-1012 may, in some cases be evaluated in a different order than illustrated in FIG. 10.

FIG. 11 is a flow diagram illustrating an example operation for determining a set of negative zero crossings in an impedance measurement, in accordance with one or more techniques of this disclosure. For convenience, FIG. 11 is described with respect to IMD 10, external device 12, and processing circuitry 14 of FIGS. 1-5. However, the techniques of FIG. 11 may be performed by different components of IMD 10, external device 12, processing circuitry 14, or by additional or alternative medical devices.

In some examples, processing circuitry 14 determines one or more respiration parameters based, at least in part, on a set of negative zero crossings. For example, processing circuitry 14 may determine a set of respiration intervals based on the set of negative zero crossings. Processing circuitry 14 may determine the set of negative zero crossings in impedance data collected by IMD 10, where the impedance data is collected during an impedance measurement. IMD 10 may, in some examples, be an ICM implanted in patient 4 that measures patient parameters for analysis to identify or monitor one or more patient conditions such as heart failure, sleep apnea, or COPD. For example, IMD 10 may perform a set of impedance measurements, where each impedance measurement produces impedance data consisting of a set of impedance values. In some cases, the impedance data may be indicative of one or more physiological functions of patient 4, such as any combination of cardiac functions, respiratory functions, and intestinal functions. For example, processing circuitry 14 may process the impedance data to determine one or more parameters (e.g., respiratory rate, respiratory rate variability, and respiratory effort) associated with respiratory cycles of the patient, as discussed in further detail below. In turn, processing circuitry 14 may analyze such parameters to identify or monitor one or more medical conditions.

As illustrated in FIG. 11, processing circuitry 14 may evaluate an impedance value n of the second set of impedance values (e.g., impedanceSignal(n)) and a corresponding impedance value of the third set of impedance values (e.g., impedanceDifference(n)) (1102) to determine if n represents a negative zero crossing (e.g., a negative zero crossing 714 as illustrated in FIG. 7). In some examples, the second set of impedance values and the first set of impedance values may be calculated based on a first set of impedance values collected by IMD 10 (e.g., raw impedance data).

At block 1104, processing circuitry 14 may determine, for each impedance value of the second set of impedance values, whether a multiplication of two consecutive impedance values of the second set of impedance values (e.g., impedanceSignal(n)·impedanceSignal(n−1)) is less than or equal to zero. In some examples, if the multiplication of two consecutive impedance values of the second set of impedance values is less than or equal to zero, this may indicate that one of impedanceSignal(n) and impedanceSignal(n−1) is negative and one of impedanceSignal(n) and impedanceSignal(n−1) is positive. Additionally, in some examples, if the multiplication of two consecutive impedance values of the second set of impedance values is less than or equal to zero, this may indicate that at least one of impedanceSignal (n) and impedanceSignal(n−1) is equal to zero. As such, by multiplying two consecutive impedance values, processing circuitry 14 may determine whether the respective consecutive impedance values represent a zero crossing event. If the multiplication of two consecutive impedance values of the second set of impedance values is not less than or equal to zero ("NO" branch of block 1104), processing circuitry 14 determines that the respective consecutive impedance values do not satisfy the condition of block 1104, and processing circuitry 14 determines that impedanceSignal(n) does not represent a negative zero crossing (1114). If the multiplication of two consecutive impedance values of the second set of impedance values is less than or equal to zero ("YES" branch of block 1104), processing circuitry 14 determines that the respective consecutive impedance values satisfy the condition of block 1104, and processing circuitry 14 proceeds to evaluate the condition of block 1106. Additionally, or alternatively, in some cases, processing circuitry may monitor impedanceSignal for sign changes at block 1104. If a sign change is detected, the condition of block 1104 is satisfied and if a sign change is not detected, the condition of block 1104 is not satisfied.

At block 1106, processing circuitry 14 may determine whether a lead impedance value (e.g., impedanceSignal(n)) of a pair of consecutive impedance values is less than zero, where the pair of consecutive impedance values (e.g., impedanceSignal(n) and impedanceSignal(n−1)) represent a zero crossing event identified by processing circuitry 14 at block 1104. If processing circuitry 14 determines that the lead impedance value is not less than zero ("NO" branch of block 1106), processing circuitry 14 determines that the respective consecutive impedance values do not satisfy the condition of block 1106, and processing circuitry 14 determines that impedanceSignal(n) does not represent a negative zero crossing (1114). If processing circuitry 14 determines that the lead impedance value is less than zero ("YES" branch of block 1106), processing circuitry 14 determines that the lead impedance value satisfies the condition of block 1106 and processing circuitry 14 proceeds to evaluate the condition of block 1108.

At block 1108, processing circuitry 14 may determine, if a difference impedance value of the third set of impedance values (e.g., ImpedanceDifference(n)) is less than a negative threshold difference value (e.g., NEGATIVE THRESHOLD). The difference impedance value may, in some cases, represent a slope associated with a lead impedance value (e.g., impedanceSignal(n)) of a pair of consecutive impedance values that processing circuitry 14 determines to be a zero crossing event in block 1104. If processing circuitry 14 determines that the difference impedance value is not less than the negative threshold difference value ("NO" branch of block 1108), processing circuitry 14 determines that the respective consecutive impedance values do not satisfy the condition of block 1108, and processing circuitry 14 determines that impedanceSignal(n) does not represent a negative zero crossing (1114). If processing circuitry 14 determines that the difference impedance value is less than the negative threshold difference value ("YES" branch of block 1108), processing circuitry 14 determines that the lead impedance value satisfies the condition of block 1108 and processing circuitry 14 proceeds to evaluate the condition of block 1110. In some examples, NEGATIVE THRESHOLD may be represented by negative auto-adjusting threshold 726 of FIG. 7.

At block 1110, processing circuitry 14 may determine whether the lead impedance value (e.g., impedanceSignal (n)) of the respective pair of consecutive impedance values that satisfies the conditions of blocks 1104-1108 is outside of a negative blanking window. To determine whether the lead impedance value is outside of the negative blanking window, processing circuitry 14 determines whether the lead impedance value is outside of a group of consecutive secondary impedance values immediately preceding the secondary impedance value n, where the group of consecutive secondary impedance values represents the negative blanking window. In some examples, the group of consecutive secondary impedance values includes a number of consecutive secondary impedance values within a range between 5 and 15 (e.g., 10). If a negative zero crossing exists within the group of consecutive secondary impedance values, processing circuitry 14 may determine that impedanceSignal(n) is not outside of the negative blanking window ("NO" branch of block 1110), determine that the condition of block 1110 is not satisfied for the secondary impedance value n, and determine that that impedanceSignal(n) does not represent a negative zero crossing (1114). If a negative zero crossing does not exist within the group of consecutive secondary impedance values, processing circuitry 14 may determine that impedanceSignal(n) is outside of the negative blanking window ("YES" branch of block 1110), determine that the condition of block 1110 is satisfied for the secondary impedance value n, and proceed to evaluate the condition of block 1112. In this way, a negative blanking window may follow each valid negative zero crossing. If a potential negative zero crossing occurs within a blanking window following a valid negative zero crossing, processing circuitry 14 may determine that the potential negative zero crossing is invalid (e.g., does not represent a valid negative zero crossing).

At block 1112, processing circuitry 14 may determine whether n is greater than one. If n is not greater than 1, processing circuitry 14 may determine that the condition of block 1112 is not satisfied and determine that impedanceSignal(n) does not represent a negative zero crossing (1114). If n is greater than 1, processing circuitry 14 may determine that the condition of blocks 1104-1112 are satisfied and determine that impedanceSignal(n) represents a negative zero crossing (1116). Subsequently, processing circuitry 14 may save the negative zero crossing (1118) in a storage device (e.g., storage device 56, storage device 84, or another storage device) as a part of the set of negative zero crossings.

Processing circuitry 14 may, in some examples, evaluate every pair of consecutive impedance values of the second set of impedance values to determine whether each respective pair of consecutive impedance values represents a negative zero crossing (e.g., a negative zero crossing 714 as illustrated in FIG. 7). The conditions of blocks 1104-1112 may, in some cases be evaluated in a different order than illustrated in FIG. 11.

Figure 12:
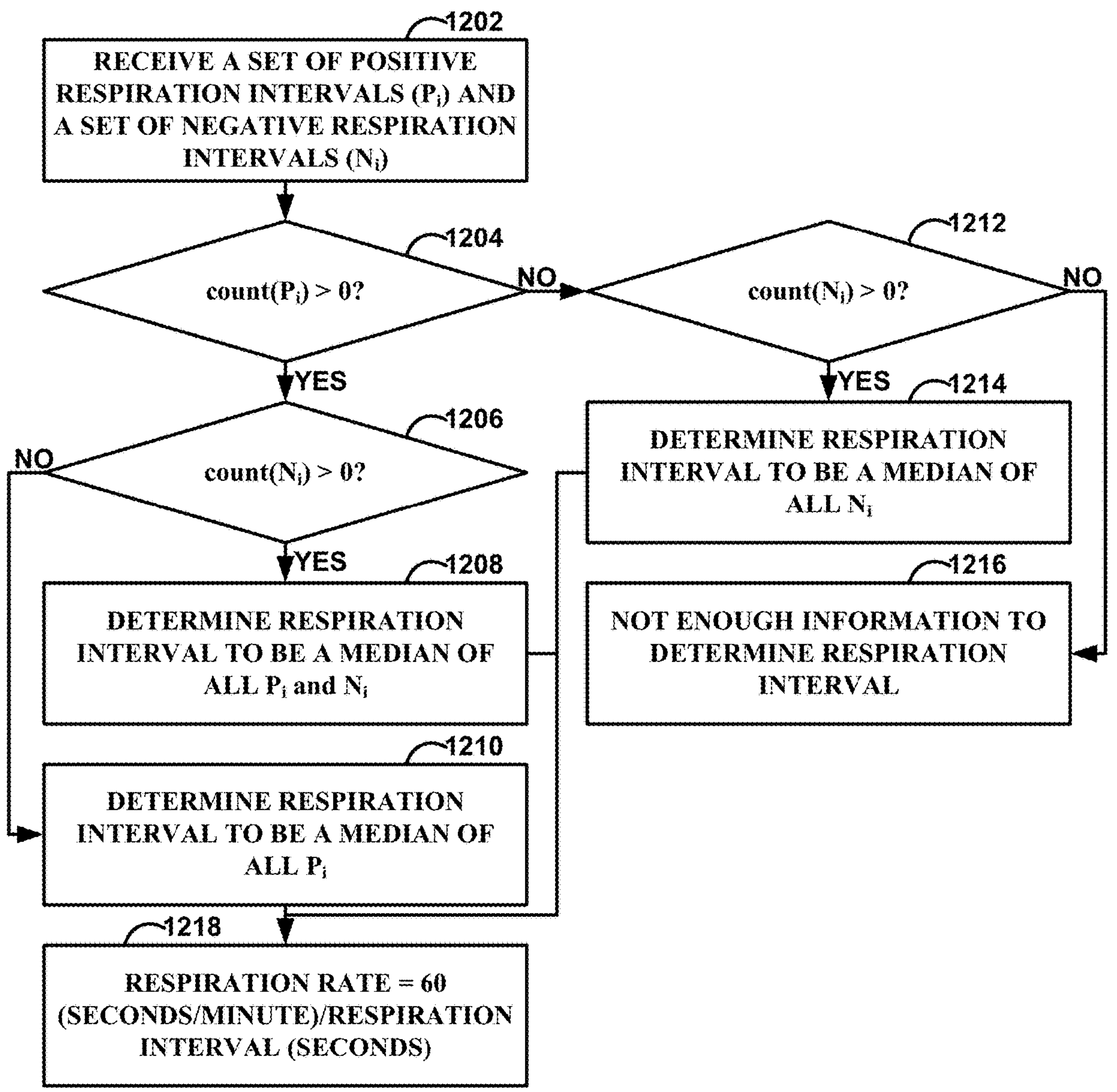
FIG. 12 is a flow diagram illustrating an example operation for determining a set of respiration intervals, in accordance with one or more techniques of this disclosure.

FIG. 12 is a flow diagram illustrating an example operation for determining a set of respiration intervals, in accordance with one or more techniques of this disclosure. For convenience, FIG. 12 is described with respect to IMD 10, external device 12, and processing circuitry 14 of FIGS. 1-5. However, the techniques of FIG. 12 may be performed by different components of IMD 10, external device 12, processing circuitry 14, or by additional or alternative medical devices.

Processing circuitry 14 may determine, or in some cases receive, a set of respiration intervals derived from positive zero crossings ($P_i$) (e.g., respiration intervals 716 of FIG. 7) and a set of respiration intervals derived from negative zero crossings ($N_i$) (e.g., respiration intervals 718 of FIG. 7) (1202). The set of respiration intervals (Pi) may be determined based on a set of positive zero crossings and the set of respiration intervals (Ni) may be determined based on a set of negative zero crossings. Subsequently, processing circuitry 14 may determine if a number of respiration intervals of the set of respiration intervals (Pi) is greater than zero (1204). If the number of respiration intervals (Pi) is greater than zero ("YES" branch of block 1204), processing circuitry 14 determines if a number of respiration intervals of the set of respiration intervals (Ni) is greater than zero (1206). Additionally, if the number of respiration intervals (Pi) is not greater than zero ("NO" branch of block 1204), processing circuitry 14 determines if a number of respiration intervals of the set of respiration intervals (Ni) is greater than zero (1212).

If, at block 1206, processing circuitry 14 determines that the number of respiration intervals (Ni) is greater than zero ("YES" branch of block 1206), processing circuitry 14 may determine a respiration interval to be a median of all respiration intervals of the set of respiration intervals (Pi) and all respiration intervals of the set of respiration intervals (Ni) (1208). Additionally, in some cases where the number of respiration intervals (Pi) is greater than zero and the number of respiration intervals (Ni) is greater than zero, processing circuitry 14 may calculate a respiration interval variation corresponding to Pi and a respiration interval variation corresponding to Ni. If processing circuitry 14 determines that the number of respiration intervals (Ni) is not greater than zero ("NO" branch of block 1206), processing circuitry 14 may determine a respiration interval to be a median of all respiration intervals of the set of respiration intervals (Pi). If, at block 1212, processing circuitry 14 determines that the number of respiration intervals (Ni) is greater than zero ("YES" branch of block 1212), processing circuitry 14 may determine a respiration interval to be a median of all respiration intervals of the set of respiration intervals (Ni) (1214). If processing circuitry 14 determines that the number of respiration intervals (Ni) is not greater than zero ("NO" branch of block 1212), processing circuitry 14 may determine that there is not enough information to determine a respiration interval associated with a respective impedance measurement (1216).

Processing circuitry 14 determines a respiration rate to be equal to 60 seconds/minute divided by the respiration interval in seconds (1218). In this way, the respiration rate may be in units of respiration cycles per minute. In other examples, processing circuitry 14 may calculate the respiration rate to be in other units of measurement such as respiration cycles per second or respiration cycles per hour.

FIG. 13 is a flow diagram illustrating an example operation for determining a peak-to-peak value, in accordance with one or more techniques of this disclosure. For convenience, FIG. 13 is described with respect to IMD 10, external device 12, and processing circuitry 14 of FIGS. 1-5. However, the techniques of FIG. 13 may be performed by different components of IMD 10, external device 12, processing circuitry 14, or by additional or alternative medical devices.

Processing circuitry 14 may, in some examples, determine a peak-to-peak value indicative of a respiration effort of patient 4. The peak-to-peak value may represent an impedance signal amplitude, or an approximation of an impedance signal amplitude corresponding to an impedance measurement performed by IMD 10. In order to determine the peak-to-peak value, processing circuitry 14 receives a set of impedance values (1302). Additionally, processing circuitry 14 receives a set of positive zero crossings and a set of negative zero crossings (1304). The set of positive zero crossings and the set of negative zero crossings may, in some examples, be represented by respective impedance values of the set of impedance values. Processing circuitry 14 may determine a group of impedance values following each positive zero crossing (1306) and determine a group of impedance values following each negative zero crossing (1308). The group of impedance values following each respective positive zero crossing may, in some cases, include a positive peak. Additionally, the group of impedance values following each respective negative zero crossing may include a negative peak. In some examples, the group of impedance values following each positive zero crossing is twenty impedance values long. Additionally, in some examples, the group of impedance values following each negative zero crossing is twenty impedance values long.

Processing circuitry 14 identifies a maximum impedance value of the group of impedance values following each positive zero crossing (1310) and identifies a minimum impedance value of the group of impedance value following each negative zero crossing (1312). Processing circuitry 14 calculates a mean maximum impedance value (1314) and calculates a mean minimum impedance value (1316), where the mean maximum impedance value represents a mean value of a set of maximum impedance values corresponding to the set of positive zero crossings and the mean minimum impedance value represents a mean value of a set of minimum impedance values corresponding to the set of negative zero crossings. In other words, the mean maximum impedance value and the mean minimum impedance value may be determined by computing a phase-locked average of positive peaks following positive zero crossings and computing a phase-locked average of negative peaks following negative zero-crossings. Subsequently, processing circuitry 14 calculates a peak-to-peak value (1318) by subtracting the mean minimum impedance value from the mean maximum impedance value. The peak-to-peak value may, in some cases, be indicative of a respiratory effort of patient 4. For example, a greater peak-to-peak value may be associated with a greater respiration effort (i.e., deeper breaths).

Figure 14:
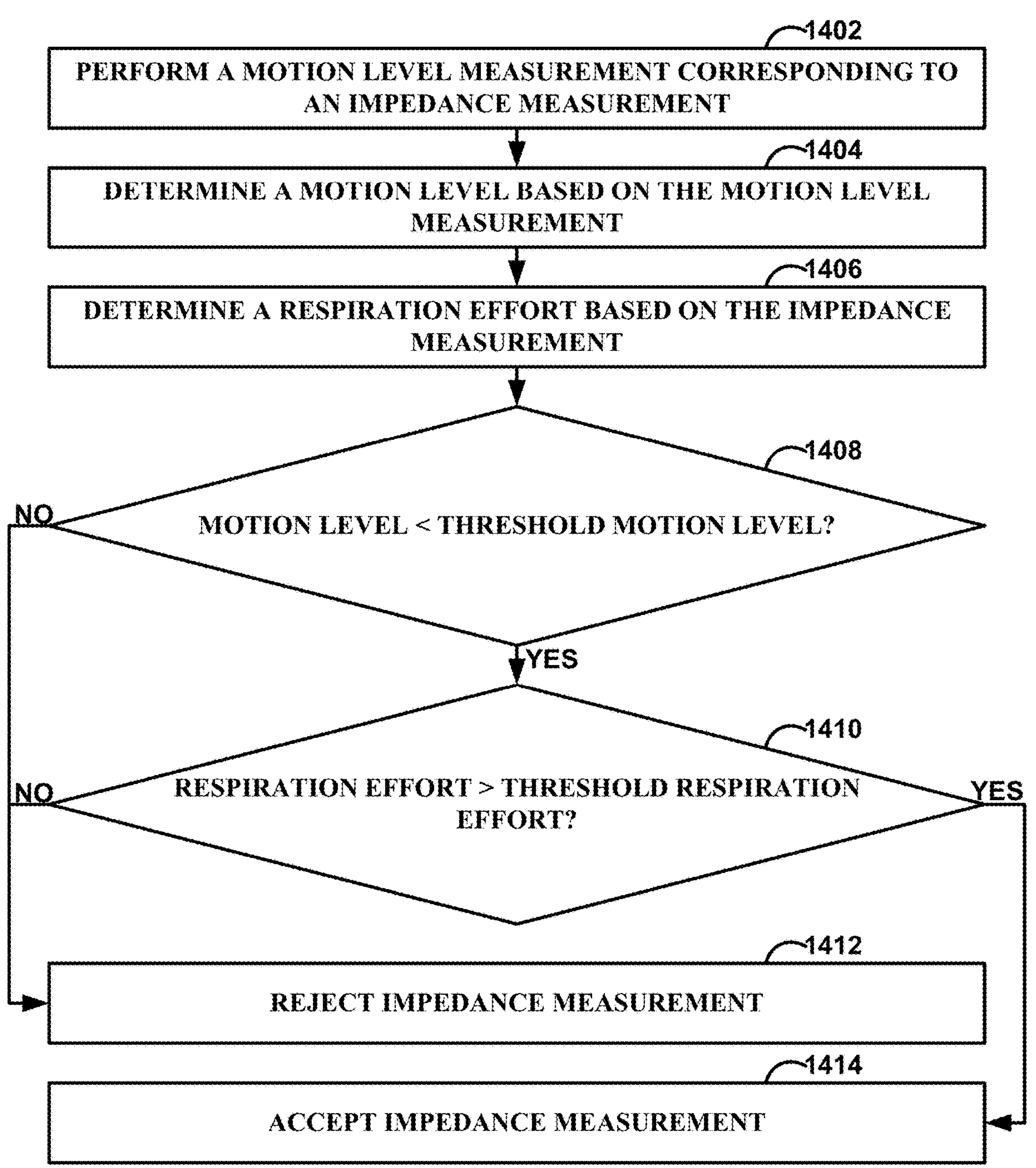
FIG. 14 is a flow diagram illustrating an example operation for determining a quality of an impedance measurement, in accordance with one or more techniques of this disclosure.

FIG. 14 is a flow diagram illustrating an example operation for determining a quality of an impedance measurement, in accordance with one or more techniques of this disclosure. For convenience, FIG. 14 is described with respect to IMD 10, external device 12, and processing circuitry 14 of FIGS. 1-5. However, the techniques of FIG. 14 may be performed by different components of IMD 10, external device 12, processing circuitry 14, or by additional or alternative medical devices.

In some examples, IMD 10, external device 12, processing circuitry 14, or any combination thereof, may evaluate a quality of an impedance measurement. In the example of FIG. 14, IMD 10 performs a motion level measurement corresponding to an impedance measurement (1402). For example, IMD 10 may perform the motion level during, shortly before, or shortly after IMD 10 performs the respective impedance measurement in order to obtain data useful for ascertaining a level of motion in patient 4. Processing circuitry 14 determines a motion level based on the motion level measurement (1404). Additionally, processing circuitry 14 determines a respiration effort based on the respective impedance measurement (1406). According to the respiration effort and the motion level, processing circuitry 14 may be configured to evaluate the quality of the impedance measurement.

At block 1408, processing circuitry 14 determines whether a motion level is less than a threshold motion level. If the motion level is not less than the threshold motion level ("NO" branch of block 1408), processing circuitry 14 rejects the impedance measurement (1412). If the motion level is less than the threshold motion level ("YES" branch of block 1408), processing circuitry 14 proceeds to evaluate whether the respiration effort is greater than a threshold respiration effort (1410). If the respiration effort is not greater than a threshold respiration effort ("NO" branch of block 1410), processing circuitry 14 rejects the impedance measurement (1412). If the respiration effort is greater than the threshold respiration effort ("YES" branch of block 1410), processing circuitry 14 accepts the impedance measurement (1414) as a quality impedance measurement. In other words, if the motion level is less than the threshold motion level and the respiration effort is greater than the threshold respiration effort, processing circuitry 14 may determine that conditions are satisfactory such that the impedance measurement may be used for determining respiratory parameters in order to identify or monitor one or more patient conditions (e.g., sleep apnea or COPD). Blocks 1408 and 1410 may be performed in any order (e.g., 1408 before 1410 or 1410 before 1408).

The techniques described in this disclosure may be implemented, at least in part, in hardware, software, firmware, or any combination thereof. For example, various aspects of the techniques may be implemented within one or more microprocessors, DSPs, ASICS, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A medical device configured to be subcutaneously inserted into a patient comprising:

a housing;

a plurality of electrodes, at least one of the plurality of electrodes being disposed on a proximal portion of the housing and at least another one of the plurality of electrodes being disposed on a distal portion of the housing;

sensing circuitry configured to perform, using the plurality of electrodes, an impedance measurement to collect a set of impedance values over a period of time outside of a medical appointment, wherein the set of impedance values is indicative of a respiration pattern of a patient; and processing circuitry configured to:

evaluate at least one of a heart rate, a patient posture, a patient activity level, an electrocardiogram (ECG), a presence or an absence of one or more arrhythmias, or data from an acoustic sensor to determine at least one of the presence of one or more arrhythmias, a change in the heart rate, a change in the patient posture, a change in the patient activity level, or detection of sound in the data from the acoustic sensor;

trigger the sensing circuitry to perform, based on the determination of the at least one of the presence of the one or more arrhythmias, the change in the heart rate, the change in the patient posture, the change in the patient activity level, or the detection of sound in the data from the acoustic sensor, the impedance measurement to collect the set of impedance values over the period of time;

identify a set of positive zero crossings based on the set of impedance values;

determine, based on the set of positive zero crossings, a first set of respiration intervals, wherein each respiration interval of the first set of respiration intervals corresponds to a respective full respiratory cycle within the respiration pattern and wherein each respiration interval of the first set of respiration intervals comprises an amount of time separating each pair of consecutive positive zero crossings of the set of positive zero crossings;

identify a set of negative zero crossings based on the set of impedance values;

determine, based on the set of negative zero crossings, a second set of respiration intervals, wherein each respiration interval of the second set of respiration intervals corresponds to a respective full respiratory cycle within the respiration pattern and wherein each respiration interval of the second set of respiration intervals comprises an amount of time separating each pair of consecutive negative zero crossings of the set of negative zero crossings;

determine, for the impedance measurement corresponding to the period of time, a value of a respiration metric based on the first set of respiration intervals and the second set of respiration intervals, wherein to determine the value of the respiration metric, the processing circuitry is configured to determine a median respiration interval of a third set of respiration intervals including the first set of respiration intervals and the second set of respiration intervals, and calculate, based on the median respiration interval, a respiration rate corresponding to the impedance measurement;

determine a median duration of the third set of respiration intervals;

determine a respiration interval duration window;

determine a number of respiration intervals of the third set of respiration intervals which define a duration outside of the respiration interval duration window;

determine that the number of respiration intervals satisfies a threshold number of respiration intervals; and determine to use the impedance measurement for the determination of the value of the respiration metric based on the determination that the number of respiration intervals satisfies the threshold number of respiration intervals.

2. The medical device of claim 1, wherein the set of impedance values is a first set of impedance values, wherein the processing circuitry is configured to:

calculate a mean impedance value of the first set of impedance values;

subtract, from each impedance value of the set of impedance values, the mean impedance value to obtain a second set of impedance values; and calculate a derivative of the first set of impedance values to obtain a third set of impedance values, and wherein the processing circuitry is configured to identify the set of positive zero crossings and identify the set of negative zero crossings further based on the second set of impedance values and the third set of impedance values.

3. The medical device of claim 2, wherein to identify the set of positive zero crossings, the processing circuitry is configured to:

identify, in the second set of impedance values, a set of pairs of consecutive impedance values, wherein a product of a first impedance value and a second impedance value of each respective pair is less than or equal to zero, and wherein each pair of consecutive impedance values of the set of pairs of consecutive impedance values corresponds to a respiration interval of the first set of respiration intervals;

determine, for each pair of the set of pairs, whether the second impedance value is greater than zero, wherein the medical device measures the first impedance value before the second impedance value; and determine, for each pair of the set of pairs, whether an impedance value of the third set of impedance values corresponding to the second impedance value is greater than a positive threshold impedance value.

4. The medical device of claim 3, wherein the processing circuitry is configured to:

determine, for each pair of the set of pairs, if the second impedance value is greater than zero and if the impedance value of the third set of impedance values corresponding to the second impedance value is greater than a positive threshold impedance value, that the respective pair represents a positive zero crossing of the set of positive zero crossings.

5. The medical device of claim 2, wherein to identify the set of negative zero crossings, the processing circuitry is configured to:

identify, in the second set of impedance values, a set of pairs of consecutive impedance values, wherein a product of a first impedance value and a second impedance value of each respective pair is less than or equal to zero, and wherein each pair of consecutive impedance values of the set of pairs of consecutive impedance values corresponds to a respiration interval of the second set of respiration intervals;

determine, for each pair of the set of pairs, whether the second impedance value is less than zero, wherein the medical device measures the first impedance value before the second impedance value; and determine, for each pair of the set of pairs, whether an impedance value of the third set of impedance values corresponding to the second impedance value is less than a negative threshold impedance value.

6. The medical device of claim 5, wherein the processing circuitry is configured to:

determine, for each pair of the set of pairs, if the second impedance value is less than zero and if the impedance value of the third set of impedance values corresponding to the second impedance value is less than a negative threshold impedance value, that the respective pair represents a negative zero crossing of the set of negative zero crossings.

7. The medical device of claim 1, wherein the processing circuitry is further configured to:

determine, for each positive zero crossing of the set of positive zero crossings, a group of impedance values following a respective positive zero crossing;

determine, for each negative zero crossing of the set of negative zero crossings, a group of impedance values following a respective negative zero crossing;

identify a maximum impedance value of the group of impedance values following each positive zero crossing;

identify a minimum impedance value of the group of impedance values following each negative zero crossing;

calculate a mean maximum impedance value;

calculate a mean minimum impedance value; and calculate a peak-to-peak value by subtracting the mean minimum impedance value from the mean maximum impedance value.

8. The medical device of claim 7, wherein the processing circuitry is further configured to:

determine that the peak-to-peak value satisfies a peak-to-peak value threshold; and determine to use the impedance measurement for the determination of the value of the respiration metric based on the determination that the peak-to-peak value satisfies the peak-to-peak value threshold.

9. The medical device of claim 8, wherein the peak-to-peak value represents a respiration effort of the patient corresponding to the impedance measurement.

10. The medical device of claim 1, wherein the processing circuitry is further configured to:

determine a motion level of the patient corresponding to the impedance measurement;

determine that the motion level satisfies a threshold motion level; and determine to use the impedance measurement for the determination of the value of the respiration metric based on the determination that the motion level satisfies the threshold motion level.

11. The medical device of claim 1, wherein the processing circuitry is configured to:

perform, at an impedance measurement rate, a set of impedance measurements including the impedance measurement, wherein the impedance measurement rate is within a range between one impedance measurement per month and ten impedance measurements per hour.

12. A method comprising:

evaluating, by processing circuitry of a medical device, at least one of a heart rate, a patient posture, a patient activity level, an electrocardiogram (ECG), a presence or an absence of one or more arrhythmias, or data from an acoustic sensor to determine at least one of the presence of one or more arrhythmias, a change in the heart rate, a change in the patient posture, a change in the patient activity level, or detection of sound in the data from the acoustic sensor;

triggering performance of, based on the at least one of the presence of the one or more arrhythmias, the change in the heart rate, the change in the patient posture, the change in the patient activity level, or the detection of sound in the data from the acoustic sensor and by sensing circuitry of a medical device subcutaneously inserted into a patient and via a plurality of electrodes of the medical device, an impedance measurement to collect a set of impedance values over a period of time, wherein the set of impedance values is indicative of a respiration pattern of a patient, and wherein at least one of the plurality of electrodes is disposed on a proximal portion of a housing of the medical device and at least another one of the plurality of electrodes is disposed on a distal portion of the housing;

identifying, by the processing circuitry of the medical device, a set of positive zero crossings based on the set of impedance values;

determining, by the processing circuitry and based on the set of positive zero crossings, a first set of respiration intervals, wherein each respiration interval of the first set of respiration intervals corresponds to a respective full respiratory cycle within the respiration pattern and wherein each respiration interval of the first set of respiration intervals comprises an amount of time separating each pair of consecutive positive zero crossings of the set of positive zero crossings;

identifying, by the processing circuitry, a set of negative zero crossings based on the set of impedance values;

determining, by the processing circuitry and based on the set of negative zero crossings, a second set of respiration intervals, wherein each respiration interval of the second set of respiration intervals corresponds to a respective full respiratory cycle within the respiration pattern and wherein each respiration interval of the second set of respiration intervals comprises an amount of time separating each pair of consecutive negative zero crossings of the set of negative zero crossing;

determining, by the processing circuitry and for the impedance measurement, a value of a respiration metric using both the set of negative zero crossings and the set of positive zero crossings, wherein determining the value of the respiration metric comprises determining a median respiration interval of a third set of respiration intervals including the first set of respiration intervals and the second set of respiration intervals, and calculating, based on the median respiration interval, a respiration rate corresponding to the impedance measurement;

determining a median duration of the third set of respiration intervals;

determining a respiration interval duration window;

determining a number of respiration intervals of the third set of respiration intervals which define a duration outside of the respiration interval duration window;

determining that the number of respiration intervals satisfies a threshold number of respiration intervals; and determining to use the impedance measurement for the determination of the value of the respiration metric based on the determination that the number of respiration intervals satisfies the threshold number of respiration intervals.

13. The method of claim 12, wherein the set of impedance values is a first set of impedance values, the method further comprising:

calculating a mean impedance value of the first set of impedance values;

subtracting, from each impedance value of the set of impedance values, the mean impedance value to obtain a second set of impedance values; and calculating a derivative of the first set of impedance values to obtain a third set of impedance values, and wherein identifying the set of positive zero crossings and identifying the set of negative zero crossings is further based on the second set of impedance values and the third set of impedance values.

14. The method of claim 13, wherein identifying the set of positive zero crossings comprises:

identifying, in the second set of impedance values, a set of pairs of consecutive impedance values, wherein a product of a first impedance value and a second impedance value of each respective pair is less than or equal to zero, and wherein each pair of consecutive impedance values of the set of pairs of consecutive impedance values corresponds to a respiration interval of the first set of respiration intervals;

determining, for each pair of the set of pairs, whether the second impedance value is greater than zero, wherein the medical device measures the first impedance value before the second impedance value; and determining, for each pair of the set of pairs, whether an impedance value of the third set of impedance values corresponding to the second impedance value is greater than a positive threshold impedance value.

15. The method of claim 14, wherein identifying the set of positive zero crossings further comprises:

determining, for each pair of the set of pairs, if the second impedance value is greater than zero and if the impedance value of the third set of impedance values corresponding to the second impedance value is greater than a positive threshold impedance value, that the respective pair represents a positive zero crossing of the set of positive zero crossings.

16. The method of claim 13, wherein identifying the set of negative zero crossings comprises:

identifying, in the second set of impedance values, a set of pairs of consecutive impedance values, wherein a product of a first impedance value and a second impedance value of each respective pair is less than or equal to zero, and wherein each pair of consecutive impedance values of the set of pairs of consecutive impedance values corresponds to a respiration interval of the second set of respiration intervals;

determining, for each pair of the set of pairs, whether the second impedance value is less than zero, wherein the medical device measures the first impedance value before the second impedance value; and determining, for each pair of the set of pairs, whether an impedance value of the third set of impedance values corresponding to the second impedance value is less than a negative threshold impedance value.

17. Non-transitory computer-readable media storing instructions for causing processing circuitry of a medical device to:

evaluate at least one of a heart rate, a patient posture, a patient activity level, an electrocardiogram (ECG), a presence or an absence of one or more arrhythmias, or data from an acoustic sensor to determine at least one of the presence of one or more arrhythmias, a change in the heart rate, a change in the patient posture, a change in the patient activity level, or detection of sound in the data from the acoustic sensor;

triggering sensing circuitry to obtain, based on the at least one of the presence of the one or more arrhythmias, the change in the heart rate, the change in the patient posture, the change in the patient activity level, or the detection of sound in the data from the acoustic sensor, an impedance measurement to collect a set of impedance values over a period of time;

identify a set of positive zero crossings based on a set of impedance values;

determine, based on the set of positive zero crossings, a first set of respiration intervals, wherein each respiration interval of the first set of respiration intervals corresponds to a respective full respiratory cycle within a respiration pattern of a patient and wherein each respiration interval of the first set of respiration intervals comprises an amount of time separating each pair of consecutive positive zero crossings of the set of positive zero crossings;

identify a set of negative zero crossings based on the set of impedance values;

determine, based on the set of negative zero crossings, a second set of respiration intervals, wherein each respiration interval of the second set of respiration intervals corresponds to a respective full respiratory cycle within the respiration pattern and wherein each respiration interval of the second set of respiration intervals comprises an amount of time separating each pair of consecutive negative zero crossings of the set of negative zero crossings;

determine, for an impedance measurement, a value of a respiration metric using both the set of negative zero crossings and the set of positive zero crossings, wherein to determine the value of the respiration metric, the instructions are configured cause the processing circuitry to determine a median respiration interval of a third set of respiration intervals including the first set of respiration intervals and the second set of respiration intervals, and calculate, based on the median respiration interval, a respiration rate corresponding to the impedance measurement;

determine a median duration of the third set of respiration intervals;

determine a respiration interval duration window;

determine a number of respiration intervals of the third set of respiration intervals which define a duration outside of the respiration interval duration window;

determine that the number of respiration intervals satisfies a threshold number of respiration intervals; and determine to use the impedance measurement for the determination of the value of the respiration metric based on the determination that the number of respiration intervals satisfies the threshold number of respiration intervals, and wherein the medical device comprises a plurality of electrodes and a housing, at least one of the plurality of electrodes being disposed on a proximal portion of the housing and at least another one of the plurality of electrodes being disposed on a distal portion of the housing, and the sensing circuitry configured to perform, using the plurality of electrodes, the impedance measurement to collect the set of impedance values over a period of time, wherein the set of impedance values is indicative of the respiration pattern of the patient.

* * * * *